US010927166B2

(12) United States Patent
Wang

(10) Patent No.: US 10,927,166 B2
(45) Date of Patent: *Feb. 23, 2021

(54) COMPOSITIONS COMPRISING AN ANTI-C5 ANTIBODY

(71) Applicant: Alexion Pharmaceuticals, Inc., Boston, MA (US)

(72) Inventor: Yi Wang, Woodbridge, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/597,040

(22) Filed: Oct. 9, 2019

(65) Prior Publication Data

US 2020/0102379 A1 Apr. 2, 2020

Related U.S. Application Data

(63) Continuation of application No. 16/152,235, filed on Oct. 4, 2018, now Pat. No. 10,479,828, which is a continuation of application No. 15/675,074, filed on Aug. 11, 2017, now Pat. No. 10,125,191, which is a continuation of application No. 11/127,438, filed on May 11, 2005, now abandoned.

(51) Int. Cl.

*A61K 39/395* (2006.01)
*C07K 16/18* (2006.01)
*A61K 39/00* (2006.01)

(52) U.S. Cl.

CPC ........ *C07K 16/18* (2013.01); *A61K 2039/505* (2013.01); *A61K 2039/54* (2013.01); *A61K 2039/543* (2013.01); *A61K 2039/544* (2013.01); *C07K 2317/55* (2013.01)

(58) Field of Classification Search

None

See application file for complete search history.

(56) References Cited

U.S. PATENT DOCUMENTS 4,228,795 A 10/1980 Babington
5,614,370 A 3/1997 Konteatis et al.
5,728,844 A 3/1998 Muller et al.
5,871,734 A 2/1999 Lobb et al.
6,316,502 B1 11/2001 Lai et al.
6,355,245 B1 3/2002 Evans et al.
6,524,836 B2 2/2003 Sheppard
6,740,655 B2 5/2004 Magee et al.
6,905,688 B2 6/2005 Rosen et al.
6,956,107 B2 10/2005 Fung et al.
6,998,468 B2 2/2006 Fung et al.
7,071,299 B2 7/2006 West et al.
7,833,525 B2 11/2010 Shenoy et al.
9,352,035 B2 5/2016 Zhou et al.
9,409,980 B1 8/2016 Zhou et al.
9,415,102 B2 8/2016 Zhou et al.
9,556,263 B2 1/2017 Zhou et al.
9,718,880 B2 8/2017 Bell et al.
9,725,504 B2 8/2017 Bell et al.
9,732,149 B2 8/2017 Bell et al.
9,925,262 B2 3/2018 Zhou et al.
10,125,191 B2 11/2018 Wang
10,479,828 B2 11/2019 Wang
10,590,189 B2 3/2020 Bell et al.
10,703,809 B1 7/2020 Bell et al.
2001/0036650 A1 11/2001 Li et al.
2002/0138857 A1 9/2002 Ghayur
2002/0172677 A1 11/2002 Lahn et al.
2002/0182260 A1 12/2002 Mak et al.
2003/0040083 A1 2/2003 Collinson et al.
2003/0124139 A1 7/2003 Esikova et al.
2003/0171259 A1 9/2003 Modi
2003/0175267 A1 9/2003 Wang et al.
2004/0014782 A1 1/2004 Krause
2004/0115194 A1 6/2004 Wang
2004/0219147 A1 11/2004 Bell
2005/0053598 A1 3/2005 Burke et al.
2005/0191298 A1 9/2005 Bell et al.
2005/0271660 A1 12/2005 Wang
2005/0282734 A1 12/2005 Kadima et al.
2007/0173444 A1 7/2007 Balu et al.
2008/0071063 A1 3/2008 Allan et al.
2008/0193466 A1 8/2008 Banerjee et al.
2009/0060906 A1 3/2009 Barry et al.
2009/0175857 A1 7/2009 Salfeld et al.
2009/0220508 A1 9/2009 Bell et al.
2010/0027882 A1 2/2010 Matsuoka
2010/0104563 A1 4/2010 Ghayer et al.

(Continued)

FOREIGN PATENT DOCUMENTS

CA 2189015 A1 11/1995
CA 2198706 A1 3/1996

(Continued)

OTHER PUBLICATIONS

Abe et al., "Contribution of Anaphylatoxin C5a to Late Airway Responses after Repeated Exposure of Antigen to Allergic Rats," The Journal of Immunology 167(8):4651-4660 (2001).
Abrahamsen et al., "Differential Mediator Release from Basophils of Allergic and Non-allergic Asthmatic Patients after Stimulation with Anti-IgE and C5a," Clinical and Experimental Allergy 31 : 368-378 (2001).
Akatsu et al., "Distribution of Rat C5a Anaphylatoxin Receptor," Microbiol. Immunol. 46(12):863-874 (2002).
American Heritage College Dictionary, 3rd Edition. Houghton Mifflin Company, Boston, p. 1085 (1997).

(Continued)

*Primary Examiner* — Phillip Gambel

(74) *Attorney, Agent, or Firm* — Nelson Mullins Riley & Scarborough LLP; Jane E. Remillard, Esq.; Jill Gorny Sloper, Esq.

(57) ABSTRACT

The present application relates to methods and compositions employing an antibody that inhibits activation of the complement system and can be used to prevent or treat a pulmonary disease or condition.

6 Claims, 16 Drawing Sheets

Specification includes a Sequence Listing.

(56) References Cited

U.S. PATENT DOCUMENTS

| | | | |
|---|---|---|---|
| 2010/0111953 A1 | 5/2010 | Ruben et al. |
| 2010/0278822 A1 | 11/2010 | Fraunhofer et al. |
| 2012/0225056 A1 | 9/2012 | Rother et al. |
| 2012/0230982 A1 | 9/2012 | Zhou et al. |
| 2012/0237515 A1 | 9/2012 | Bell et al. |
| 2014/0056888 A1 | 2/2014 | Zhou et al. |
| 2016/0215044 A1 | 7/2016 | Zhou et al. |
| 2016/0244516 A1 | 8/2016 | Bell et al. |
| 2016/0272700 A1 | 9/2016 | Zhou et al. |
| 2016/0376355 A1 | 12/2016 | Bell et al. |
| 2017/0015741 A1 | 1/2017 | Bell et al. |
| 2017/0151328 A1 | 6/2017 | Zhou et al. |
| 2017/0349652 A1 | 12/2017 | Bell et al. |
| 2017/0355759 A1 | 12/2017 | Wang |
| 2019/0092843 A1 | 3/2019 | Wang |
| 2020/0199211 A1 | 6/2020 | Bell et al. |

FOREIGN PATENT DOCUMENTS

| | | | |
|---|---|---|---|
| EP | 0649468 A1 | 4/1995 |
| WO | 95/29697 A1 | 11/1995 |
| WO | 98/11066 A1 | 3/1998 |
| WO | 98/18827 A1 | 5/1998 |
| WO | 03/084524 A1 | 10/2003 |
| WO | 2004/022096 A1 | 3/2004 |
| WO | 2005/011614 A2 | 2/2005 |
| WO | 2006/122257 A2 | 11/2006 |

OTHER PUBLICATIONS

Bjornson et al., "Complement is Activated in the Upper Respiratory Tract During Influenza Virus Infection," Am. Rev. Respir. Dis. 143:1062-1066 (1991).

Blease et al., "Chemokines and Their Role in Airway Hyperreactivity," Respir. Res. 1 :54-61 (2000).

Boulet et al., "Airway Hyperresponsiveness, Inflammation, and Subepithelial Collagen Deposition in Recently Diagnosed vs. Long-standing Mild Asthma," American Journal of Respiratory and Critical Care Medicine 162:1308-1313 (2000).

Chakir et al., "Airway Remodeling-associated Mediators in Moderate to Severe Asthma: Effect ** of Steroids on TGF-f3, IL-11, IL-17, and Type I and Type III Collagen Expression," J. Allergy Clin. Immunol. 111 :1293-1298 (2003).

Chenoweth et al., "Demonstration of Specific C5a Receptor on Intact Human Polymorphonuclear Leukocytes," Proc. Natl. Acad. Sci. USA 75(8):3943-3947 (1978).

Chung, "Cytokines in Chronic Obstructive Pulmonary Disease," Eur. Respir. J. 18(34):505-59s (2001).

Cieslewicz et al., "The Late, but not Early, Asthmatic Response is Dependent on IL-5 and Correlates with Eosinophil Infiltration," J. Clin. Invest. 104:301-308 (1999).

Collard et al., "Complement Activation Following Oxidative Stress," Molecular Immunology 36:941-948 (1999).

Cummings, J. et al., "Influence of polysorbate 80 (Tween 80) and etoposide (VP-16-213) on the pharmacokinetics and urinary excretion of adriamycin and its metabolites in cancer patients," Cancer. Chemother. Pharmacol., vol. 17 (1):80-84 (1986).

Czermak et al., "Complement, Cytokines, and Adhesion Molecule Expression in Inflammatory Reactions," Proceedings of the Association of American Physicians 110(5):306-312 (1998).

Desai et al., "Demonstration of C5 Cleaving Activity in Bronchoalveolar Fluids and Cells: A ** Mechanism of Acute and Chronic Alveolitis," Journal of Experimental Pathology 1(3):201-216 (1984).

Drouin et ai, "Expression of the Complement Anaphylatoxin C3a and C5a Receptors on Bronchial Epithelial and Smooth Muscle Cells in Models of Sepsis and Asthma," The Journal of Immunology 166:2025-2032 (2001).

Ex parte Yi Wang; Appeal 2017-003979,Decision on Appeal, mailed Jan. 22, 2018.

Fitch et al., "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass," Circulation 100:2499-2506 (1999).

Frank, "Complement: A Brief Review," J. Allergy Clin. Immunol. 84(4,1 ):411-420 (1989).

Gerard et al., "Complement in Allergy and Asthma," Current Opinion in Immunology 14:705-708 (2002).

Glovsky et al., "Is Complement Activation a Factor in Bronchial Asthma?," Int. Arch. Allergy Immunol.118:330-332 (1999).

Gonczi et al., "The Severity of Clinical Symptoms in Ragweed-allergic Patients is Related to ** the Extent of Ragweed-induced Complement Activation in their Sera," Allergy 51 :1110-1114 (1997).

Hawlisch et al., "Teh Anaphylatoxins Bridge Innate and Adaptive Immune Responses in Allergic Asthma," Molecular Immunology 41 :123-131 (2004).

Hogaboam et al., "Mannose-binding Lectin Deficiency Alters the Development of Fungal ** Asthma: Effects on Airway Response, Inflammation, and Cytokine Profile," Journal of Leukocyte Biology 75:805-814 (2004).

Holgate et al., "The Bronchial Epithelium as a Key Regulator of Airway Inflammation and Remodelling in Asthma," Clinical and Experimental Allergy 29:90-95 (1999).

Hopken et al., "Teh C5a Chemoattractant Receptor Mediates Mucosal Defence to Infection," Nature 383:86-89 (1996).

Humbles et al., "A role for the C3a anaphylatoxin receptor in the effector phase of asthma," Letters to Nature, vol. 406; pp. 998-1001 (2000).

Irvin et al., "Airways Hyperreactivity and Inflammation Produced by Aerosolization of Human C5A des arg 1-3," Am. Rev. Respir Dis. 134:777-783 (1986).

Jagels et al., "C3a and C5a Enhance Granulocyte Adhesion to Endothelial and Epithelial Cell ** Monolayers: Epithelial and Endothelial Priming is Required for C3a-induced Eosinophil Adhesion," Immunopharmacology 46:209-222 (2000).

Kaplan, Mariana, "Eculizumab," Current Opinion in Investigational Drugs, vol. 3(7); pp. 1017-1023 (2002).

Karp et al., "Identification of Complement Factor 5 as a Susceptibility Locus for Experimental Allergic Asthma," Nature Immunology 1( 3)221-226 (2000).

Kodani et al., "Intratracheal Administration of Anaphylatoxin C5a Potentiates Antigen-induced Pulmonary Reactions Through the Prolonged Production of Cysteinyl-leukotrienes," Immunopharmacology 49:263-274 (2000).

Krug et al., "Complement Factors C3a and C5a are Increased in Bronchoalveolar Lavage Fluid after Segmental Allergen Provocation in Subjects with Asthma," Am. J. Respir. Crit. Care Med. 164:1841-1843 (2001).

Kwaan HC et al., "Enhancement of fibrinolysis and thrombolysis by polysorbate 80 (tween 80)", Experientia, vol. 23 (4):261-262 (1967).

Larsen et al., "A Differential Effect of C5a and C5a des Arg inthe Induction of Pulmonary Inflammation," Am. J. Pathol. 100:179-192 (1980).

Lukacs et al., "Complement-dependent Immune Complex-induced Bronchial Inflammation and Hyperreactivity," Am. J. Physiol. Lunch Cell Mol. Physiol. 280:L512-L518 (2001).

Maruo et al., "Generation of Anaphylatoxins Through Proteolytic Processing of C3 and C5 by House dust Mite Protease," J. Allergy Clin. Immunol. 100:253-260 (1997).

Matis and Rollins, Complement-specific antibodies: Designing novel anti-inflammatories, Nature Medicine, vol. 1 No. 8, (1995).

Mattos et al., "Matrix Metalloproteinase-9 Expression in Asthma," Chest 122:1543-1552 (2002).

Moongkarndi et al., "Immunological and functional properties of two monoclonal antibodies against human C5," Immunobiol. vol. 165, p. 323 (1983).

Moongkarndi et al., "Monoclonal antibodies against the fifth component of human complement," Immunobiol, vol. 162; paqe 397(1982).

Mueller et al., "Humanized Porcine VCAM-Specific Monoclonal Antibodies With Chimeric ** IgG2/G4 Constant Regions Block Human Leukocyte Binding to Porcine Endothelial Cells," Molecular Immunology, vol. 34(6), pp. 141-452 (1997).

(56) References Cited

OTHER PUBLICATIONS

Nageta et al., "Activation of Human Serum Complement with Allergens," J. Allergy Clin. Immunol.80:24-32 (1987).
Nagy et al., "The Development of Asthma in Children Infected with Chlamydia pneumoniae is Dependent on the Modifying Effect of Mannose-binding Lectin," J. Allergy Clin. Immunol. 112(4):729-734 (2003).
Neurogen Reports Phase lia Clinical Trial Results for Oral Asthma Drug, Press Release dated (2004).
O'Byrne et al., "Reassessing the Th2 Cytokine Basis of Asthma," Trends in Pharmacological Sciences 25(5):244-248 (2004).
Peng et al., "Role of C5 in the Development of Airway Inflammation, Airway ** Hyperresponsiveness, and Ongoing Airway Response," The journal of Clinical Investigation 115(6):1590-1600(2005).
Peng, et al., Blocking Intrapulmonary Activation of Complement Cascade on the Development ** of Airway Hyperresponsiveness: Utility in sight? J. Allergy & Clin. Immunol. 117(3):720 (2006).
Peng et al. "Contribution of complement component C5 in the development of airway ** inflammation, maintaining airway hyperresponsivenesss and sustaining an ongoing asthmatic attack," Mol. Immunol. 41(2-3):292 (2004).
Robbins et al., "Complement Activiation by Cigarette Smoke," L254-L259 (1990).
Taube et al., "Inhibition of Complement Activation Decreases Airway Inflammation and Hyperresponsiveness," Am. J. Respir. Crit. Car Med. 168:1333-1341 (2003).
Teran et al., "Identification of Neutrophil Chemotactic Factors in Bronchoalveolar Lavage Fluid of Asthmatic Patients," Clinical and Experimental Allergy 27:396-405 (1997).
Thoman, C., "The versatility of polysorbate 80 (Tween 80) as an ionophore," J. Pharm Sci., vol. 88(2):258-260 (1999).
Thomas et al., "Inhibition of Complement Activity by Humanized Anti-C5 Antibody and Single-Chain Fv.," Molecular Immunology, vol. 33(17/18), pp. 1389-1401 (1996).
Varsano et al., "Generation of Complement C3 and Expression of Cell Membrane Complement Inhibitory Proteins by Human Bronchial Epithelium Cell Line," Thorax 55:364-369 (2000).
Wang et al., "Amelioration of Luplike Autoimmune Disease in NZBIWF, Mice after Treatment ** with a Blocking Monoclonal Antibody Specific for Complement Component C5," Proc. Natl. Acad. Sci. USA 93:8563-8568 (1996).
Wang et al., "Anti-C5 Monoclonal Antibody Therapy Prevents Collagen-induced Arthritis and Ameliorates Established Disease," Proc. Natl. Acad. Sci. USA 92:8955-8959 (1995).
Whiss, PA, "Pexelizumab Alexion," Current Opinion Investig. Drugs, vol. 3(6); pp. 870-877 (2002) (abstract).
Wills-Karp et al., "Interleukin-13: Central Mediator of Allergic Asthma," Science 282:2258-2261 (1998).

2 days after aerosol treatment

FIG. 10

Example of Suitable Formulations

Formulation 1

- Mab 1- 30 mg/ml
- 10 mM sodium phosphate
- 150 mM NaCl
- pH 6-8
- 0.001 to 0.02% Tween 80 v/v
- physiologic osmolality Formulation 2

- 20mM Histidine
- 50mM Glycine
- 3% (w/v) Sorbital
- 1.5% (w/v) Mannitol
- pH 6-8
- 0.001 to 0.02% Tween 80
- 40mg/ml-200mg/ml
- physiologic osmolality Particle Size Distribution

FIG. 13

Nebulization and Delivery Efficiency

| | Sonik LDI Eculizumab | Pari LC Jet Plus Eculizumab | Pari LC Jet Plus Pulmozyme |
|---|---|---|---|
| Respirable fraction (%) | 44.91 – 59.63 | 71.88 – 74.21 | 47.8 (1 – 5 μm) |
| Nebulizer efficiency (%) | 11.24 – 19.91 | 42.51 – 52.46 | 51.4 |
| Delivery (%) | 6.70 – 8.94 | 31.55 – 37.71 | 24.6 (1 – 5 μm) |

Respirable fraction: the fraction of the droplets delivered to the exit from the mouthpiece in the range of 0.625 – 5 μm

Nebulizer efficiency: the fraction of the dose initially placed in the nebulizer that reaches the exit from the mouthpiece

Delivery: the fraction of the initial dose that reaches the exit from the mouthpiece in the size range of 0.625 – 5 μm Eculizumab Aerosolization

SDS-PAGE Analysis

4-20% TG, 1.5mm, 10 Well, Non Reduced
Reference NDG #1383 page 38-42

Pari-Jet Air

M12 1 2 3 4 5 6 7 8 9

| Lane | Sample | load (ug) | Purity(%) | % Peak Response |
|---|---|---|---|---|
| | MW marker | NA | NA | N/A |
| 1 | Ecu Ref Std | 1.5 | 99.3 | N/A |
| 2 | TR-CTRL-1 (30mg/mL) | 1.5 | 99.1 | 102.7 |
| 3 | 16FEB05, F1D2C1 | 1.5 | 97.7 | 99.8 |
| 4 | 16FEB05, F1D2C2 | 1.5 | 98.5 | 98.6 |
| 5 | 16FEB05, F1D2C3 | 1.5 | 96.8 | 99.3 |
| 6 | 16FEB05, F1D2C4 | 1.5 | 94.3 | 94.1 |
| 7 | 16FEB05, F1D2C5 | 1.5 | 88.9 | 92.3 |
| 8 | 16FEB05, F1D2F | 1.5 | N/A | N/A |
| 9 | Blank | N/A | N/A | N/A |

FIG. 15

Eculizumab Aerosolization

SEC HPLC Purity Summaries

| | 15 Feb 05 | | 16Feb 05 | |
|---|---|---|---|---|
| | Sonik LDI | Pari Jet Air | Sonik LDI | Pari Jet Air |
| F1P1-W1 | 99.1 | 98.4 | 99.0 | 98.4 |
| F1P2-W1 | 99.2 | 99.2 | 98.2 | 98.5 |
| F1P3-W1 | 99.1 | 99.2 | 99.1 | 99.1 |
| F1P4-W1 | 95.7 | NA | 93.8 | n/a |
| F1C1-W1 | [95.6] | 97.5 | 94.2 | 97.7 |
| F1C2-W1 | [96.1] | 98.2 | 95.8 | 98.5 |
| F1C3-W1 | [94.9] | 96.9 | [96.3] | 96.8 |
| F1C4-W1 | [93.0] | 94.0 | 95.2 | 94.3 |
| F1C5-W1 | [90.8] | 89.3 | [92.7] | 88.9 |
| [Peak responses < 90%] | | | | |

SEQUENCE LISTING

```
<160> NUMBER OF SEQ ID NOS: 3

<210> SEQ ID NO 1
<211> LENGTH: 248
<212> TYPE: PRT
<213> ORGANISM: Artificial Sequence
<220> FEATURE:
<223> OTHER INFORMATION: SEQ ID NO: 8 incorporated by reference,
      sequence derived from murine and human

<400> SEQUENCE: 1

Met Ala Asp Ile Gln Met Thr Gln Ser Pro Ser Ser Leu Ser Ala Ser
1               5                   10                  15

Val Gly Asp Arg Val Thr Ile Thr Cys Gly Ala Ser Glu Asn Ile Tyr
            20                  25                  30

Gly Ala Leu Asn Trp Tyr Gln Arg Lys Pro Gly Lys Ala Pro Lys Leu
        35                  40                  45

Leu Ile Tyr Gly Ala Thr Asn Leu Ala Asp Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Asn Val Leu Asn Thr
                85                  90                  95

Pro Leu Thr Phe Gly Gln Gly Thr Lys Val Glu Ile Lys Arg Thr Gly
            100                 105                 110

Gly Gly Gly Ser Gly Gly Gly Gly Ser Gly Gly Gly Gly Ser Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Ile Phe Ser Asn Tyr Trp Ile
145                 150                 155                 160

Gln Trp Val Arg Gln Ala Pro Gly Gln Gly Leu Glu Trp Met Gly Glu
                165                 170                 175
```

```
Ile Leu Pro Gly Ser Gly Ser Thr Glu Tyr Thr Glu Asn Phe Lys Asp
            180                 185                 190

Arg Val Thr Met Thr Arg Asp Thr Ser Thr Ser Thr Val Tyr Met Glu
        195                 200                 205

Leu Ser Ser Leu Arg Ser Glu Asp Thr Ala Val Tyr Tyr Cys Ala Arg
    210                 215                 220

Tyr Phe Phe Gly Ser Ser Pro Asn Trp Tyr Phe Asp Val Trp Gly Gln
225                 230                 235                 240

Gly Thr Leu Val Thr Val Ser Ser
                245


<210> SEQ ID NO 2
<211> LENGTH: 230
<212> TYPE: PRT
<213> ORGANISM: Artificial Sequence
<220> FEATURE:
<223> OTHER INFORMATION: SEQ ID NO: 12 incorporated by reference (with
      leader peptide, or first 19 amino acid residues, removed);
      sequence derived from murine and human

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr
225                 230


<210> SEQ ID NO 3
<211> LENGTH: 214
<212> TYPE: PRT
<213> ORGANISM: Artificial Sequence
<220> FEATURE:
```

-continued

```
<223> OTHER INFORMATION: SEQ ID NO: 15 incorporated by reference (with
      leader peptide, or first 22 amino acid residues, removed),
      sequence derived from murine and human

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

COMPOSITIONS COMPRISING AN ANTI-C5 ANTIBODY

RELATED APPLICATIONS

This application is a continuation of U.S. patent application Ser. No. 16/152,235, filed on Oct. 4, 2018, which is a continuation of U.S. patent application Ser. No. 15/675,074 filed on Aug. 11, 2017, which is now U.S. Pat. No. 10,125,191, issued on Nov. 13, 2018, and which is a continuation of U.S. patent application Ser. No. 11/127,438, filed on May 11, 2005. The entire contents of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Oct. 8, 2019, is named AXJ_102CPCN3_SL.txt and is 6979 bytes in size.

BACKGROUND

Asthma, bronchitis and emphysema are known collectively as Chronic Obstructive Pulmonary Diseases. These diseases are characterized as generalized airways obstruction, especially of small airways, associated with varying degrees of symptoms of chronic bronchitis, asthma, and emphysema. These diseases may often coexist in an individual, and it may be difficult to determine the primary cause of an airway obstruction. Airway obstruction is defined as an increased resistance to airflow during forced expiration. Obstruction of large airways may also occur in these diseases, particularly in asthma. Currently available therapy for asthma remains problematic. Similarly, improved therapy is also desirable for treating or preventing other pulmonary diseases, for example lung cancers.

Effective delivery to a patient is a critical aspect of any successful drug therapy. Various routes of delivery exist, and each has its own advantages and disadvantages. Oral drug delivery of pills, capsules, elixirs, and the like is perhaps the most convenient method, but many drugs are degraded in the digestive tract before they can be absorbed. Subcutaneous injection is frequently an effective route for systemic drug delivery, including the delivery of proteins, but enjoys a low patient acceptance. Since injection of drugs one or more times a day can frequently be a source of poor patient compliance, a variety of alternative routes of administration have also been developed, including transdermal, intranasal, intrarectal, intravaginal, and pulmonary delivery. Thus, it is desirable to improve drug delivery methods and compositions, particularly for antibody-based therapeutics in treating or preventing pulmonary diseases.

SUMMARY

Accordingly, this application provides compositions and methods suitable for delivering antibody-based therapeutics. These antibody-based therapeutics can be particularly useful in preventing or treating pulmonary diseases or conditions such as for example asthma. Examples of antibodies useful in this application include anti-C5 antibody or antibodies that inhibit activation of the complement cascade, for example, the antibodies as described in U.S. Pat. No. 6,355,245. For example, U.S. Pat. No. 6,355,245 discloses a humanized (CDR grafted) scFv designated 5G1.1 scFv CB (SEQ ID NO:8), wherein CDR L1 is amino acid residues 26-36 of SEQ ID NO:8, CDR L2 is amino acid residues 52-58 of SEQ ID NO:8, CDR L3 is amino acid residues 91-99 of SEQ ID NO:8, CDR H1 is amino acid residues 152-161 of SEQ ID NO:8, CDR H2 is amino acid residues 176-192 of SEQ ID NO:8, H3 is amino acid residues 225-237 of SEQ ID NO:8. SEQ ID NO:8 from U.S. Pat. No. 6,355,245 corresponds to SEQ ID NO:1 in the present application. Accordingly, in one embodiment, the anti-C5 antibody comprises a variable light chain CDR1 comprising amino acid residues 26-36 of SEQ ID NO:1, a variable light chain CDR2 comprising amino acid residues 52-58 of SEQ ID NO:1, a variable light chain CDR3 comprising amino acid residues 91-99 of SEQ ID NO:1, a variable heavy chain CDR1 comprising amino acid residues 152-161 of SEQ ID NO:1, a variable heavy chain CDR2 comprising amino acid residues 176-192 of SEQ ID NO:1, and a variable heavy chain CDR3 comprising amino acid residues 225-237 of SEQ ID NO:1.

U.S. Pat. No. 6,355,245 also discloses a humanized (CDR grafted, not framework altered) Fd designated 5G1.1 VH+IGHRLC (SEQ ID NO:12), as well as a humanized (CDR grafted, not framework altered) light chain designated 5G1.1 VL+012 (SEQ ID NO:15). SEQ ID Nos: 12 and 15 from U.S. Pat. No. 6,355,245 correspond to SEQ ID Nos: 2 and 3, respectively, in the present application. Accordingly, in one embodiment, the antibody comprises a heavy chain variable region amino acid sequence corresponding to amino acid 1 through amino acid 122 of SEQ ID NO:2. In another embodiment, the antibody comprises a light chain variable region amino acid sequence corresponding to amino acid 1 through amino acid 108 of SEQ ID NO:3. In another embodiment, the antibody comprises a heavy chain variable region amino acid sequence corresponding to amino acid 1 through amino acid 122 of SEQ ID NO:2 and a light chain variable region amino acid sequence corresponding to amino acid 1 through amino acid 108 of SEQ ID NO:3.

In addition to antibodies, other therapeutics are also contemplated to be employed with the compositions and methods of the present application, for example, the chimeric complement inhibitor proteins as described in U.S. Pat. No. 5,627,264. Certain preferred embodiments employ pexelizumab or eculizumab as the antibody therapeutic. In certain embodiments, the methods suitable for delivering antibody-based therapeutics for treating or preventing pulmonary diseases are not designed for systemic delivery of the therapeutics, and therefore, systemic effect of the therapeutics may not be observed using these methods.

A first aspect of the application provides a method for preventing or treating a pulmonary disease or condition in a subject comprising administering to the subject a therapeutically effective amount of an antibody that inhibits activation of the complement cascade or blocks the function of one or more subsequently activated components of the complement system. In certain embodiments, an additional active agent is also administered to the same subject. Administration of the antibody and the additional active agent may occur simultaneously or sequentially in either order. In certain embodiments, the antibody and the additional active agent can be administered to the subject via the same delivery method or route, for example, by inhalation. In alternative embodiments, the antibody and the additional active agent can be administered to the subject via different delivery methods or routes, for example, the antibody delivered by inhalation and the additional active agent by injection or by oral intake.

A second aspect of the application provides an aerosol composition comprising an antibody that inhibits activation of the complement cascade, wherein the composition is suitable for preventing or treating a pulmonary disease or condition in a subject. The antibody is formulated in a composition suitable for aerosolization. The antibody may be formulated in combination with an additional active agent, and the combination formulation is suitable for aerosolization. Alternatively, the antibody and an additional active agent may be formulated separately, such that they will be combined after aerosolization occurs or after being administered to a subject.

A third aspect of the application provides a nebulization composition comprising an antibody that inhibits activation of the complement cascade, wherein the composition is suitable for preventing or treating a pulmonary disease or condition in a subject. The antibody is formulated in a composition suitable for nebulization. Similarly, the antibody may be formulated in combination with an additional active agent, and the combination formulation is suitable for nebulization. Alternatively, the antibody and an additional active agent may be formulated separately, such that they will be combined after nebulization occurs or after being administered to a subject.

A further aspect of the application provides a biopharmaceutical package comprising an antibody that inhibits activation of the complement cascade and a nebulizer, wherein the package is suitable for preventing or treating a pulmonary disease or condition in a subject. The biopharmaceutical package may further comprise an active agent in addition to the antibody. The biopharmaceutical package may also comprise instructions for use.

Pulmonary diseases or conditions contemplated by the application include, but are not limited to, asthma, bronchial constriction, bronchitis, a chronic obstructive pulmonary disease (COPD), interstitial lung diseases, lung malignancies, α-1 anti-trypsin deficiency, emphysema, bronchiectasis, bronchiolitis obliterans, sarcoidosis, pulmonary fibrosis, and collagen vascular disorders.

The timing of administering a therapeutic to a subject can vary, for example, depending on the identity of the subject or the pulmonary disease or condition to be treated or prevented, or both. For example, the administration may occur before the manifestation of the pulmonary condition (e.g., pre-asthmatic attack), during the manifestation of the pulmonary condition (e.g., during the asthmatic attack), or after the manifestation of the pulmonary condition (e.g., post-asthmatic attack).

An antibody of the present application can be specific to C5 such that it prevents the cleavage of C5 into C5a and C5b. The antibody can be specific to the C5 convertase. Alternatively, the antibody may be specific to a component of the complement system, for example, C5a, C5b, or C5b-9, and the antibody specific to the component preferably inhibits the component's function, for example, by blocking the component's binding to its respective receptor, or by blocking its function in activating the subsequent signaling or events in the complement cascade. Certain embodiments employ eculizumab or pexelizumab, or both. An antibody or antibody therapeutic of the present application can be a full length immunoglobulin, a monoclonal antibody, a chimeric antibody (e.g., a humanized antibody), a single chain antibody, a domain antibody, an Fab fragment, or an antibody having an Fab fragment and a mutated Fc portion. In certain embodiments, the mutated Fc portion does not activate complement, or the mutation(s) in the Fc portion decreases the Fc portion's ability to activate complement. An antibody of the present application may be produced or processed in bulk and packaged in an ampule made of a suitable material (e.g., glass or plastic) at different doses.

An additional active agent (or an active agent in addition to the antibody therapeutic) of the present application can be another antibody therapeutic (e.g., an anti-IgE antibody such as Xolair® or omalizumab, an anti-IL-4 antibody or an anti-IL-5 antibody), an anti-IgE inhibitor (e.g., Singulair® or montelukast sodium), a sympathomimetic (e.g., albuterol), an antibiotic (e.g., tobramycin), a deoxyribonuclease (e.g., pulmozyme), an anticholinergic drug (e.g., ipratropium bromide), a corticosteroid (e.g., dexamethasone), a β-adrenoreceptor agonist, a leukotriene inhibitor (e.g., zileuton), a 5 Lipoxygenase inhibitor, a PDE inhibitor, a CD23 antagonist, an IL-13 antagonist, a cytokine release inhibitor, a histamine H1 receptor antagonist, an anti-histamine, an anti-inflammatory agent (e.g. cromolyn sodium) or a histamine release inhibitor.

An example of formulation suitable for aerosolization or nebulization of an antibody is in physiologic osmolarity (e.g., between 280 and 320 mM) at a suitable pH (e.g., pH 6 to 8). A formulation of the present application may further comprise an excipient, for example polysorbate 80 which can be used at 0.0015 to 0.02%.

A nebulizer of the present application can be a jet air nebulizer (e.g., Pari LC® Jet Plus or Hudson T UP-DRAFT® II), an ultrasonic nebulizer (e.g., MABISMist II), a vibrating mesh nebulizer (e.g., MicroAir® by Omron) and a shockwave nebulizer (Evit Labs Sonik LDI20).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A: Representative DCP results indicating the longitudinal changes of sRaw. After aerosol challenge with 5% OVA for 10 min, the appearance of EAR was observed at 15 min, followed by the LAR at 5 h. FIG. 2B: Three critical points during the course of disease. Checkpoint 1: Anti-C5 mAb was given by i.p. injection on days 25, 29 and 31. Analysis of lower airway functions and quantification of airway inflammation were evaluated 5 h after aerosol challenge of 5% OVA on day 32. Checkpoint 2: Anti-C5 mAb was given by i.p. injection on day 33, after recovery from the first airway response on day 32. AHR was assessed by evaluating the changes of RL and Cdyn from baseline in response to aerosol Mch challenge on day 35. Checkpoint 3: C5 inhibition was given by either i.v. or aerosol administration of BB5.1 during EAR on day 35. Lower airway function was determined during the peak of LAR, 5 h after 5% OVA provocation.

Figure 8A:
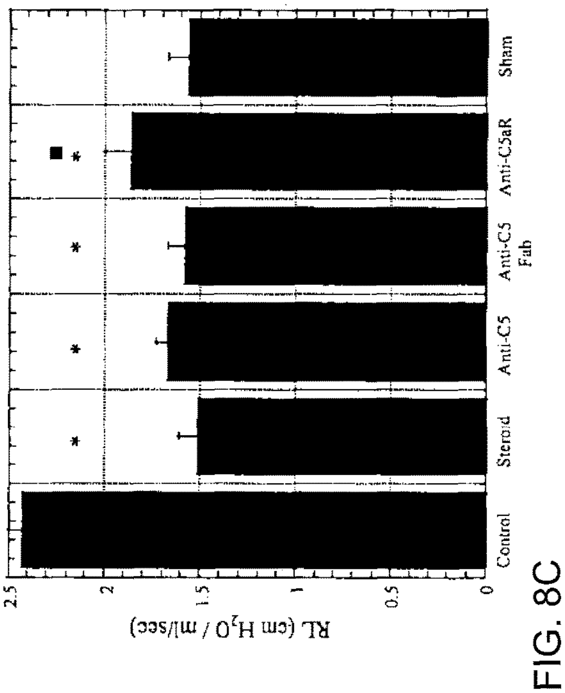
FIGS. 8A-8D show contributions of intrapulmonary C5 activation at checkpoint 3.
Figure 8B:
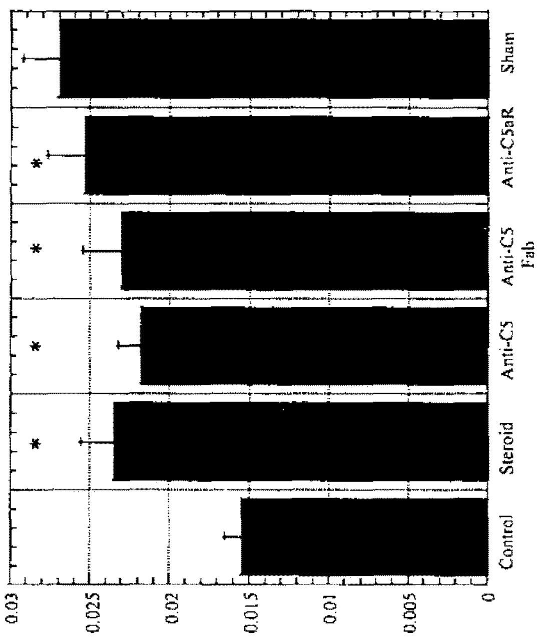

Results represent data pooled from 3 separate experiments with identical experimental procedures. Animals were aerosol challenged with 5% OVA and randomized. During EAR, animals were then given aerosol administration of one of the indicated treatments through a jet nebulizer. Sham-immunized mice were treated with aerosol PBS. All animals were trachea cannulated for the measurement of RL (FIG. 8A) and Cdyn (FIG. 8B) 5 h after the OVA provocation. BALF WBC counts (FIG. 8C) and proMMP9 (FIG. 8D) were analyzed in the majority of animals. The data from control mAb (n=15) and control sIgG treated mice (n=4) were pooled together. Except anti-C5 Fab (n=3), n=6-19 animals in all other cohorts.

Figure 9:
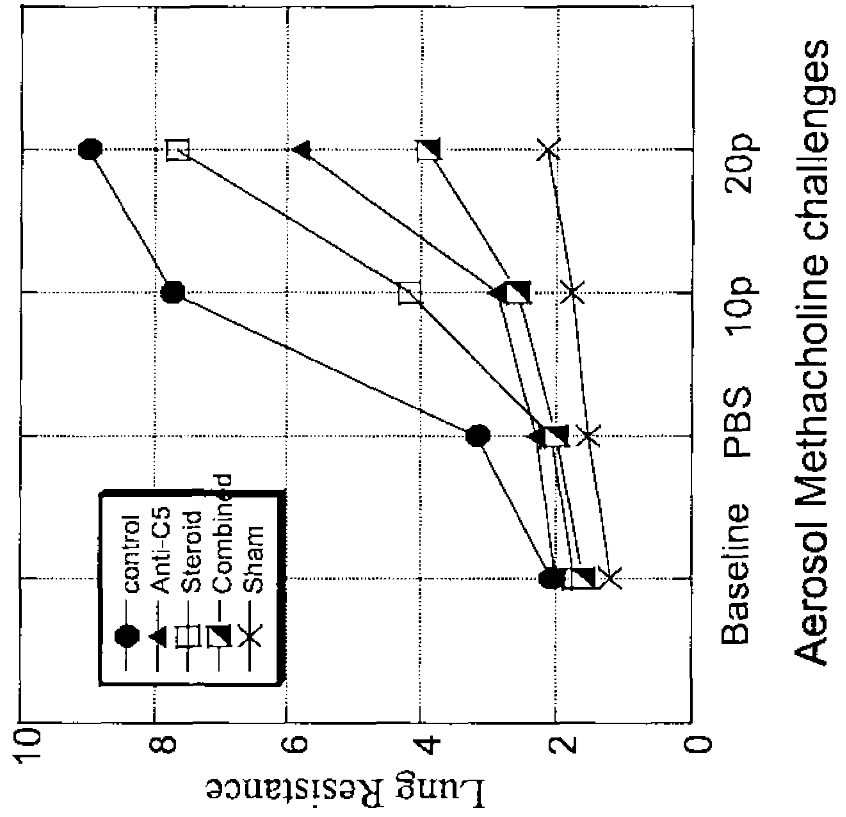

FIG. 9 shows the result of combined therapy on the development of AHR in subjects with established airway inflammation. The results were obtained based on checkpoint 2 study as described herein. Treatment was delivered on day 32 by nebulization instead of i.p. Mch challenge occurred on day 35. For anti-C5, BB5.1 at 3 mg/ml was subjected to nebulization for 10 minutes. The steroid at 2 mg/ml was nebulized for 10 minutes. For the combination, the final concentration was 3 mg/ml for BB5.1 and 2 mg/ml for the steroid, which was subjected to nebulization for 10 minutes.

FIG. 10 shows exemplary formulations suitable for nebulization of an antibody. Specifically, "Formulation 1" is 30 mg/ml of an antibody, 10 mM sodium phosphate, 150 mM NaCl, and 0.001 to 0.02% Tween 80 by volume. "Formulation 2" is 40-200 mg/ml of an antibody, 20 mM histidine, 50 mM glycine, 3% (w/v) sorbital, 1.5% (w/v) mannitol, and 0.001 to 0.02% Tween 80.

Figure 11:
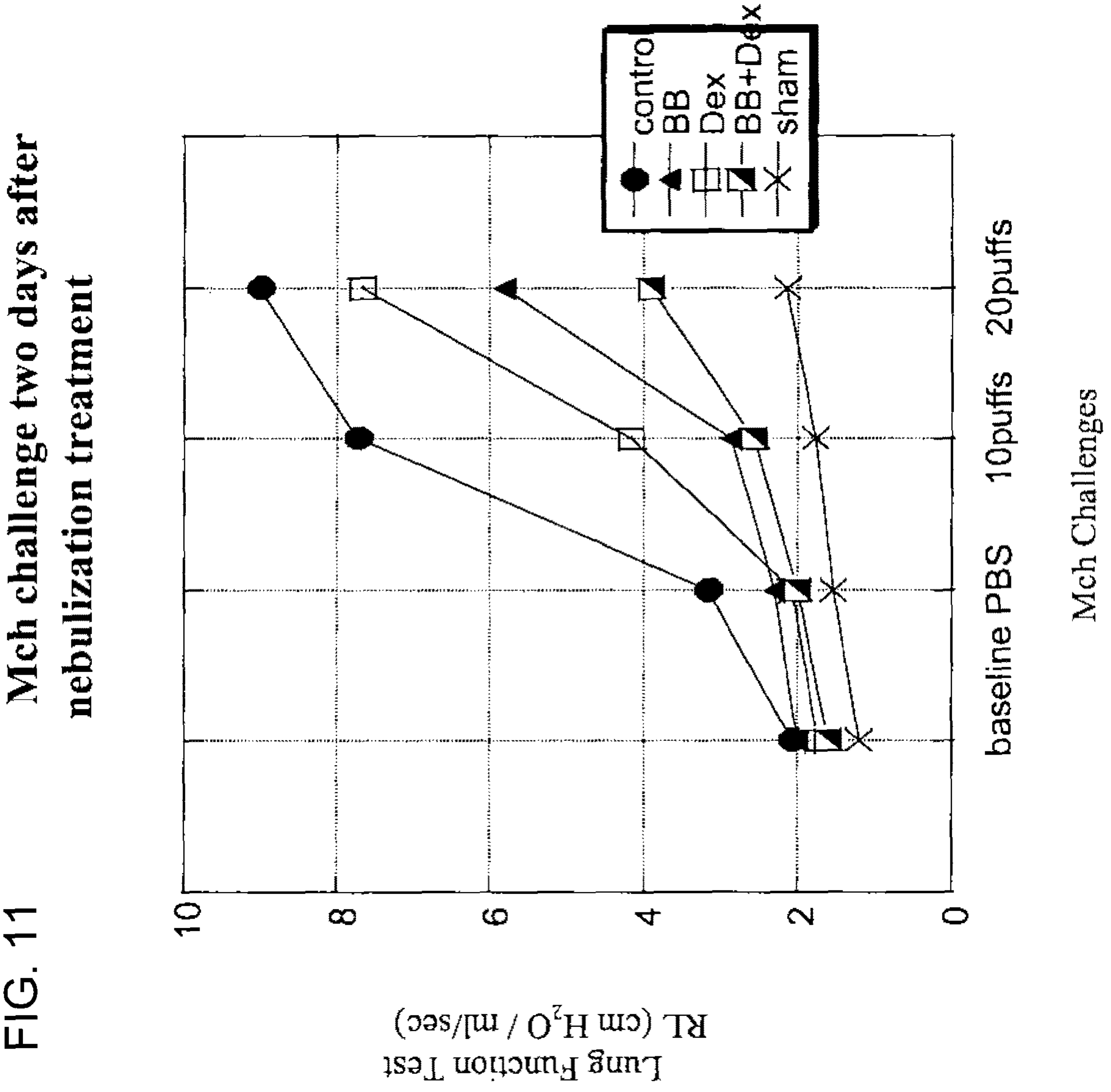

FIG. 11 shows the result of Mch challenge two days after nebulization treatment.

Figure 12:
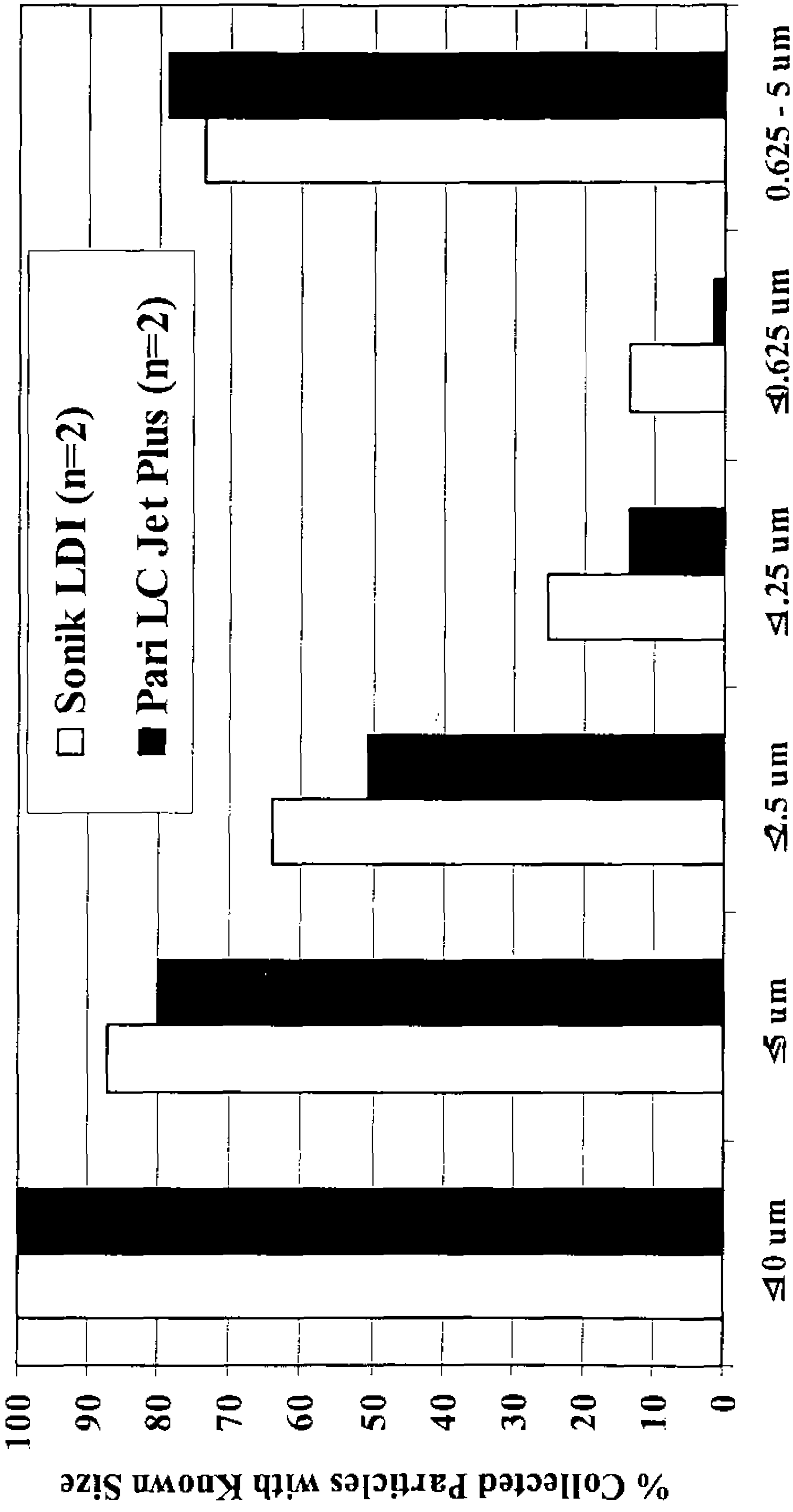

FIG. 12 shows the particle size distribution.

FIG. 13 shows nebulization and delivery efficiencies.

Figure 14:
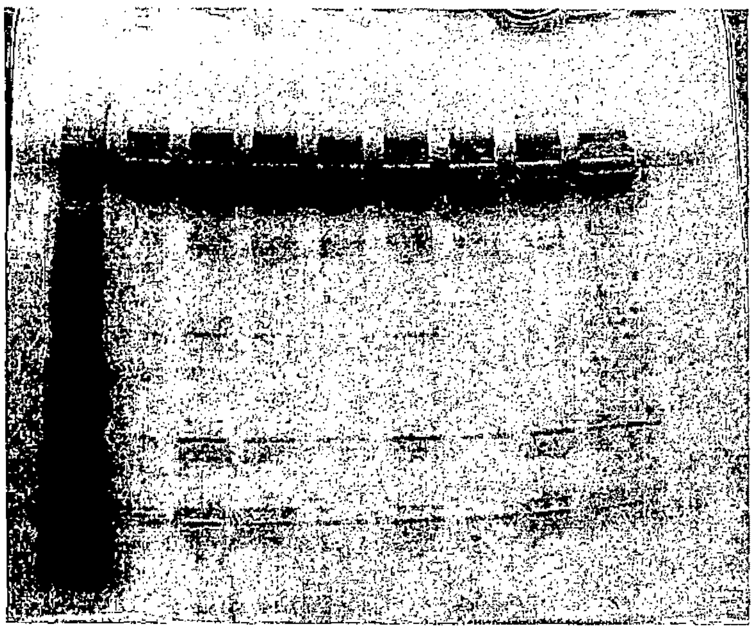

FIG. 14 shows SDS-PAGE analysis of aerosolized eculizumab.

FIG. 15 shows SEC HPLC analysis of aerosolized eculizumab using two different nebulizers.

Figure 16:
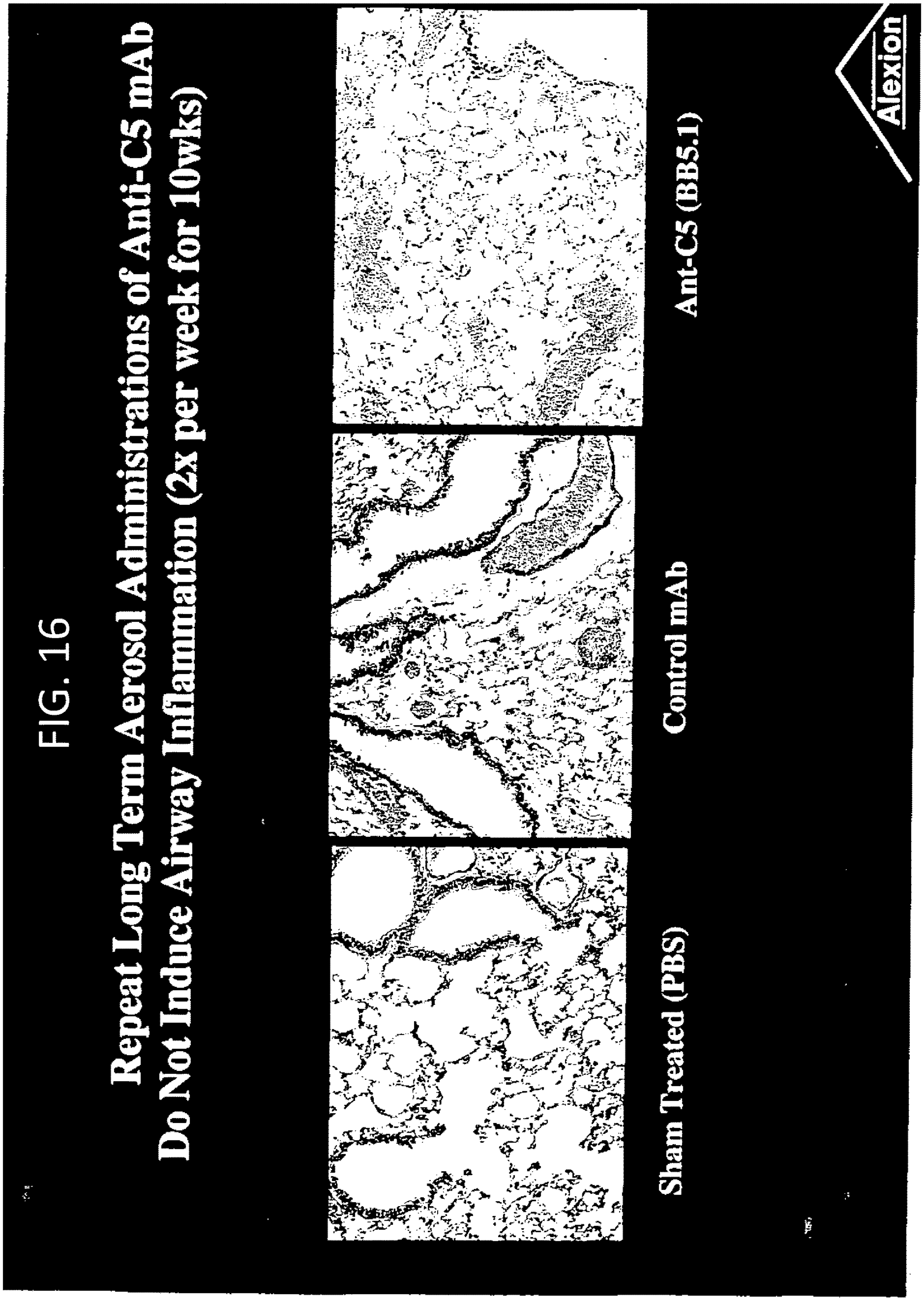

FIG. 16 shows that repeated long term aerosol administrations of anti-C5 monoclonal antibody do not induce airway inflammation. The mice here were subject to 10-week treatments: sham mice were treated with PBS for 10 min twice per week for 10 weeks; control mice were treated with HFN7.1 (an isotype-matched mouse antibody) for 10 min by nebulization, also twice a week for 10 weeks; the anti-C5 antibody (BB5.1) treated mice were treated with BB5.1 for 10 min by nebulization, also twice a week for 10 weeks.

DETAILED DESCRIPTION OF THE APPLICATION

Overview

The present application abbreviates certain terms as follows:

AHR: airway hyper-responsiveness; BALF: bronchoalveolar lavage fluid; Cdyn—dynamic lung compliance; C5aR: C5a receptor; C5d: C5 deficient; C5s: C5 sufficient; DCP: double chamber plethysmograph; EAR: Early phase airway response; IC: immune complexes; LAR: Late phase airway response; Mch: methacholine; rmC5a: recombinant mouse C5a; RL: lung resistance; sRaw: Specific airway resistance; sIgG: serum IgG.

The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components, and while they differ in their initial steps, they converge and share the same "terminal complement" components (C5 through C9) responsible for the activation and destruction of target cells.

The classical complement pathway is typically initiated by antibody recognition of and binding to an antigenic site on a target cell. The alternative pathway is usually antibody independent, and can be initiated by certain molecules on pathogen surfaces. Both pathways converge at the point where complement component C3 is cleaved by an active protease (which is different in each pathway) to yield C3a and C3b. Other pathways activating complement attack can act later in the sequence of events leading to various aspects of complement function.

C3a is an anaphylatoxin (see discussion below). C3b binds to bacterial and other cells, as well as to certain viruses and immune complexes, and tags them for removal from the circulation. (C3b in this role is known as opsonin.) The opsonic function of C3b is considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone (Fearon, in Intensive Review of Internal Medicine, 2d ed. Fanta and Minaker, eds. Brigham and Women's and Beth Israel Hospitals, 1983).

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways (Wurzner, et al., Complement Inflamm. 8:328-340, 1991). This property of C3b is regulated by the serum protease Factor I, which acts on C3b to produce iC3b. While still functional as opsonin, iC3b cannot form an active C5 convertase.

C5 is a 190 kDa beta globulin found in normal serum at approximately 75 μg/ml (0.4 μM). C5 is glycosylated, with about 1.5-3 percent of its mass attributed to carbohydrate. Mature C5 is a heterodimer of a 999 amino acid 115 kDa alpha chain that is disulfide linked to a 656 amino acid 75 kDa beta chain. C5 is synthesized as a single chain precursor protein product of a single copy gene (Haviland et al. J. Immunol. 1991, 146:362-368). The cDNA sequence of the transcript of this gene predicts a secreted pro-C5 precursor of 1659 amino acids along with an 18 amino acid leader sequence.

The pro-C5 precursor is cleaved after amino acid 655 and 659, to yield the beta chain as an amino terminal fragment and the alpha chain as a carboxyl terminal fragment, with four amino acids deleted between the two. C5a is cleaved from the alpha chain of C5 by either alternative or classical C5 convertase as an amino terminal fragment comprising the first 74 amino acids of the alpha chain. Approximately 20 percent of the 11 kDa mass of C5a is attributed to carbohydrate. The cleavage site for convertase action is at or immediately adjacent to amino acid residue 733 of the 1659-amino acid pro-C5 precursor sequence with an 18-amino acid leader sequence (SEQ ID NO:2 as described in U.S. Pat. No. 6,355,245). A compound that would bind at or adjacent to this cleavage site would have the potential to block access of the C5 convertase enzymes to the cleavage site and thereby act as a complement inhibitor.

C5 can also be activated by means other than C5 convertase activity. Limited trypsin digestion (Minta and Man, J. Immunol. 1977, 119:1597-1602; Wetsel and Kolb, J. Immunol. 1982, 128:2209-2216) and acid treatment (Yamamoto and Gewurz, J. Immunol. 1978, 120:2008; Damerau et al., Molec. Immunol. 1989, 26:1133-1142) can also cleave C5 and produce active C5b.

C5a is another anaphylatoxin. C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

Pulmonary Diseases or Conditions, and the Complement System

Certain pulmonary diseases or conditions such as asthma can be characterized by a combination of chronic airway inflammation, airway obstruction and airway hyper-responsiveness (AHR) to various stimuli. It is thought to be mediated primarily by adaptive immune responses including allergen-specific $CD4^+$ T cells, Th2 cytokines, and allergen specific IgE leading to pulmonary inflammation and AHR. Complement and its activated components, which form a central core of innate immune defense against bacterial, viral and fungal invasions (Nagy et al., J. Allergy. Clin. Immunol. (2003) 112:729-734; Kasamatsu et al., Arerugi (1993) 42:1616-1622; Bjornson et al., Am. Rev. Respir. Dis. (1991) 143:1062-1066), can be activated through the classical pathway, alternative pathway and the lectin pathway (Lachmann, Res. Immunol. (1996) 147:69-70). All three activation pathways converge at complement component C5 prior to the generation of C5a and C5b-9, both of which induce potent biological responses including tissue injury, inflammation, anaphylatoxic responses, and cell lysis at very low concentrations (Takafuji et al., Int. Arch. Allergy Immunol. (1994) 104 Suppl. 1:27-29). In addition, C5 can be activated after allergen exposure (Nagata et al., J. Allergy Clin. Immunol. (1987) 80:24-32). Recent data from animal models of allergic asthma suggest that activated complement components, such as C5a, provide a critical link between innate and adaptive immunity (Karp et al., Nat. Immunol. (2000) 1:221-226). However, controversies remain in the art regarding the involvement of C5 and its activated components in the pathogenesis of asthma (Karp et al., supra; Gerard et al., Curr. Opin. Immunol. (2002) 14:705-708; Abe et al., J. Immunol. (2001) 167:4651-4660; Lukacs et al., Am. J. Physiol. Lung Cell. Mol. Physiol. (2001) 280(3):L512-L518).

Several experimental models for bronchial asthma have indicated that C5 and its activated components are involved in the development of airway inflammation and bronchoconstriction (or bronchial constriction). Inhibition studies with various complement inhibitors markedly reduced AHR or airway inflammation in rodents (Abe et al., supra; Lukacs et al., supra). The potential involvement of C5 activation was also extended to clinical observations that the severity of clinical symptoms was correlated with the extent of C5 activation (Gonczi et al., Allergy (1997) 52:1110-1114). On the other hand, studies have shown that C5 deficiency (C5d) leads to increased susceptibility to allergen-induced AHR in mice, and this finding is supported by evidence of decreased production of IL-12, a key Th1 cytokine reported to modulate the pathogenesis of asthma (Karp et al., supra). The key question at the center of the debate is whether C5 and its activated components are pro-inflammatory or anti-inflammatory during the sensitization phase and the effector phase of the pathogenesis as suggested respectively from studies of C5d animals (Karp et al., supra) and experiments with intervention during the course of disease (Abe et al., supra; Lukacs et al., supra). In addition, another key issue is whether intrapulmonary-activated complement components play a significant role in the pathogenesis and overcome the potential anti-inflammatory effect of activated C5 components on the adaptive immune system (Karp et al., supra).

The present application relates to the study of the contribution of C5 and its activated components at three critical points during the course of disease, which outlines the key mechanisms of this essential component of the innate immune system in the pathogenesis of asthma. Comprehensive analyses of lower airway function and quantification of multiple parameters of airway inflammation have been conducted. As described herein, the study shows that C5 contributes to the initiation of airway inflammation, demonstrates the critical contribution of C5 in the development of AHR in animals with established airway inflammation and the significant role of activated C5 components in sustaining an on-going airway response to allergen challenge.

The pathophysiological hallmark necessary for the development of asthma-like symptoms is airway inflammation. Individuals with a genetic predisposition may have modulated adaptive immune responses to environmental exposures, including activation of allergen-specific $CD4^+$ T cells, polarization of Th2 cytokines, such as IL-4 and IL-5, which are critically involved in the production of allergen-specific IgE and the recruitment of eosinophils (Cieslewicz et al., J. Clin. Invest. (1999) 104:301-308). More recently, IL-13 was identified as a key player in the pathogenesis, and reported to be both necessary and sufficient to induce the airway response in animals (Wills-Karp et al., Science (1998) 282:2258-2261). As shown by the study described herein, the broad spectrum of anti-inflammatory activities of corticosteroid, including modulating the Th2 cytokine profile (FIGS. 7 A and B) and blocking the recruitment of inflammatory cells into lower airways (FIG. 3D), correlates with its potent antiasthmatic activity. Consistent with its anti-inflammatory activities reported earlier (Wang et al., Proc. Natl. Acad. Sci. U.S.A (1996) 93:8563-8568), C5 inhibition at checkpoint 1 resulted in significantly less airway inflammation without significant impact on the adaptive immune system's responses to allergen exposures. Further, C5d animals developed a similar degree of airway inflammation as that developed by C5s animals. One possible explanation is that airways are directly exposed to allergens and infections. These exposures may activate other complement components, such as C3a, which has very similar proinflammatory properties (Takafuji et al., Int. Arch. Allergy Immunol. (1994) 104 Suppl. 1:27-29; Nagata et al., J. Allergy Clin. Immunol. (1987) 80:24-32), and was known to contribute to the pathogenesis (Gerard et al., Curr. Opin. Immunol. (2002) 14:705-708). The data provided in the present application indicate that activated C5 components are critically involved but are not necessary for the initiation of airway inflammation, which requires the activation of adaptive immune responses to aerosol exposures of allergen (Cieslewicz et al., supra). However, at checkpoints 2 and 3 when airway inflammation was already well established, the data described herein indicate that C5 inhibition has similar or better efficacy than corticosteroid in ameliorating airway inflammation and improving lower airway functions (see, e.g., FIGS. 4-8).

Figures 4A, 4B, 4C, 4D:
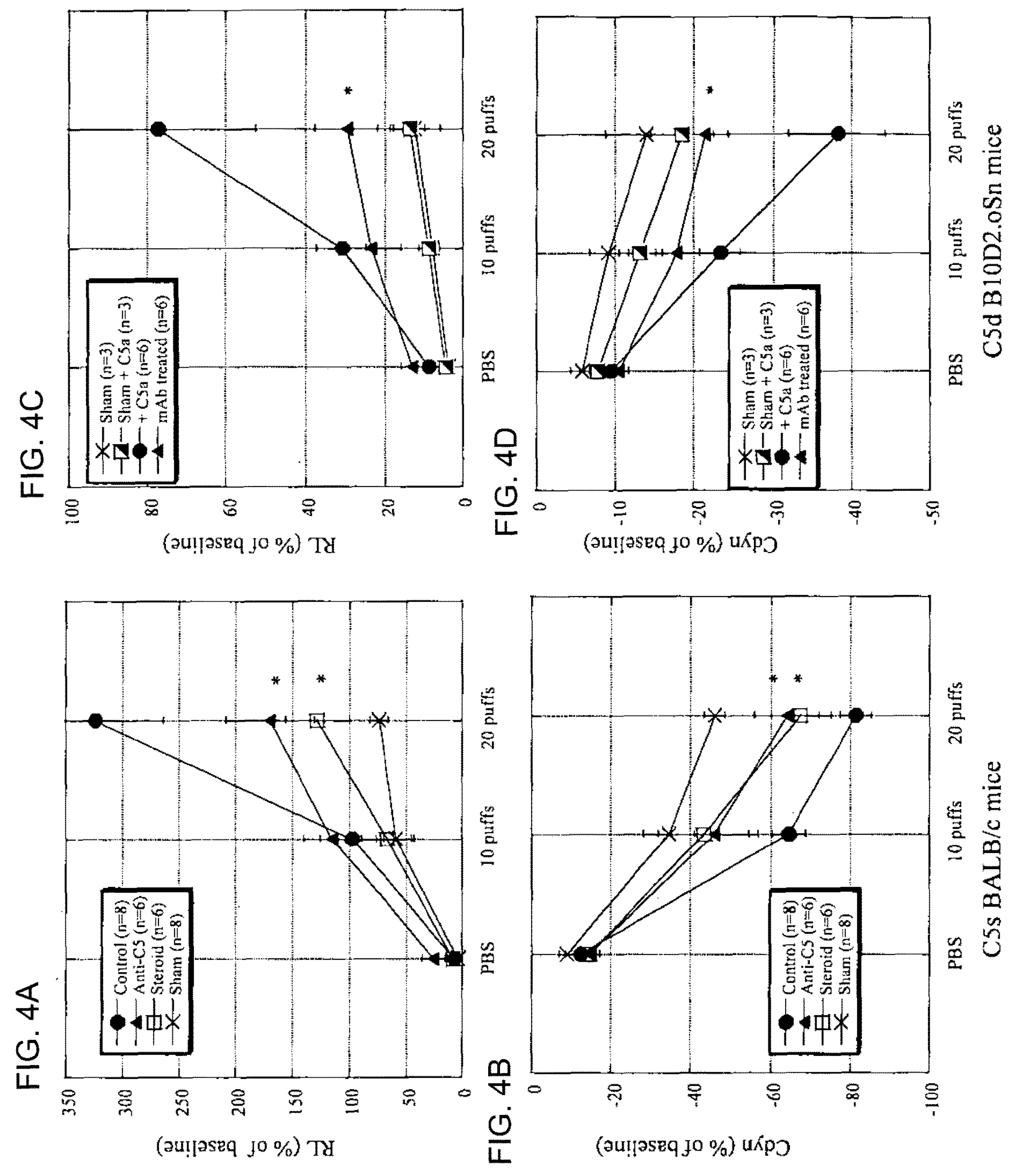
FIGS. 4A-4D show contributions of C5 at checkpoint 2, the development of AHR. C5s BALB/cByJ mice (FIGS. 4A-4B) and C5d B10D2oSn mice (FIGS. 4C-4D) were immunized with OVA in identical manner (FIG. 4B). Animals were randomized and given (i.p.) the indicated treatment on day 33. On day 35, aerosol Mch challenges were administered through a trachea cannula during measurement of RL (FIGS. 4A-4C) and Cdyn (FIGS. 4B-4D). Changes in RL and Cdyn are expressed as a percentage of baseline after each aerosol challenge. Subgroups of C5d mice with or without OVA immunization were reconstituted (i.v.) with 200 μg of rmC5a 3 hours prior to Mch challenges. For C5s BALB/c mice, * indicates $p<0.05$ when comparing either steroid or anti-C5 mAb treated animals with control mAb treated animals. For C5d B10D2oSn mice, * indicates $p<0.05$ when comparing the mAb treated animals (n=6) given either control mAb (n=3) or anti-C5 mAb (n=3) with OVA immunized C5d B10D2oSn mice reconstituted with rmC5a. There are no statistical differences between C5d animals treated with control mAb and anti-C5 mAb.

The second hallmark of asthma, the development of AHR in response to non-specific stimuli, was selected as another critical checkpoint. By pre-screening several strains of C5s and C5d mice, the genetic influences on the function of muscarinic acetylcholine receptor responsible for the intrinsic AHR (De Sanctis et al., Am. J. Respir. Crit. Care Med. (1997) 156:S82-S88; Levitt et al., FASEB J. (1988) 2:2605-2608.) are eliminated from the study described herein. Using animals that do not have intrinsic AHR, C5 inhibition is shown to be sufficient to prevent the development of AHR to aerosol Mch challenges in C5s BALB/c mice with established airway inflammation (FIGS. 4 A and B) while reconstitution of C5d B10D2oSn mice with rmC5a restored AHR, also in the presence of established airway inflammation (FIGS. 4 C and D). These data suggest that C5, most likely C5a, serves as a direct link between the innate immune responses and the key components of the airways responsible for AHR. C5aR was found on airway smooth muscle cells and airway epithelia (Drouin et al., J. Immunol. (2001) 166:2025-2032). Although the direct interaction of activated C5 components, in particular C5a, with receptors on airway smooth muscles and epithelium was demonstrated previously (Irvin et al., Am. Rev. Respir. Dis. (1986) 134:777-783; Larsen, Annu. Rev. Immunol. (1985) 3:59-85.), the data provided herein indicate that the maintenance of AHR depends upon complex interactions among airway epithelia, airway smooth muscle cells, inflammatory cells and their inflammatory mediators as suggested by minimal impact on the functions of lower airways during Mch challenges after systemic reconstitution (i.v.) of sham B10D2.oSn mice with rmC5a (FIGS. 4 C and D).

The on-going airway responses after aerosol allergen provocation, serve as the third critical checkpoint in the study described herein. The development of EAR and LAR together with massive production and release of multiple inflammatory mediators provide a good opportunity to examine the complex interaction of activated C5 components with other components of innate and adaptive immune responses and their role in pathogenesis. The data described herein demonstrate that C5 inhibition by either anti-C5 monoclonal antibody (mAb) or its Fab fragment achieved similar in vivo efficacy in ameliorating intrapulmonary inflammatory activities as well as in improving functions of lower airways.

Figure 8C:
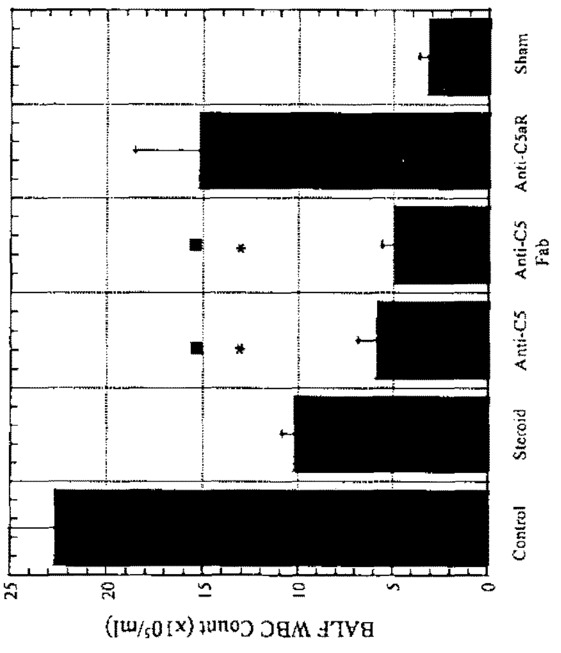
Figure 8D:
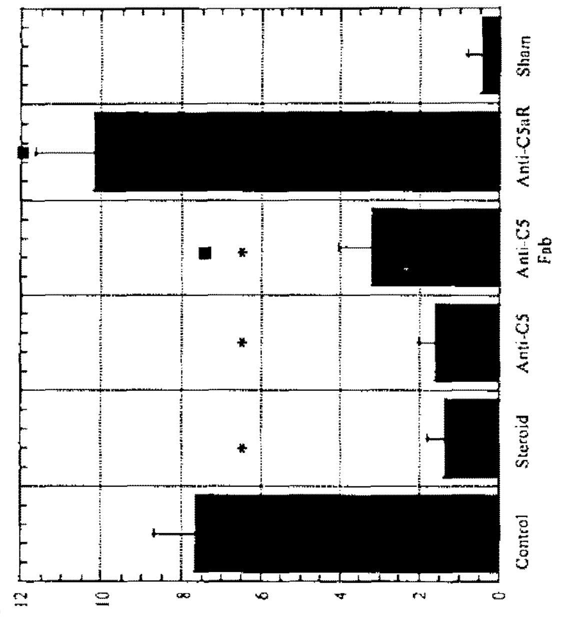

The data here also suggest that in the presence of airway inflammation, activated C5 components function as the key regulators of the downstream inflammatory cascade. This regulatory effect is demonstrated by its ability to influence the migration of inflammatory cells into airway lumen as well as the activation and the release of multiple harmful mediators corresponding to the significant changes of lower airway functions at checkpoint 3. C5a is probably the most potent activator of inflammatory cells (Takafuji et al., supra) and C5aR has been identified on circulating leukocytes, mast cells, macrophages, and endothelial cells (Chenoweth et al., Proc. Natl. Acad. Sci. U.S.A. (1978) 75:3943-3947). The disassociation of significant improvement of lower airway functions with significant presence of intrapulmonary inflammatory activities after anti-C5aR sIgG treatment is consistent with the hypothesis that the direct engagement of C5a with its receptors expressed on airway smooth muscle cells and epithelia is, in part, responsible for airway constriction (Irvin et al., supra). The data also indicate that the chemotactic activity and cell activation properties of C5b-9 (Czermak et al., Am. J. Pathol. (1999) 154:1513-1524) are responsible for the significant intrapulmonary inflammatory activities in the absence of C5aR engagement. In the presence of established airway inflammation and IC, C5b-9 can sufficiently regulate the downstream inflammatory cascade by triggering releases of multiple mediators such as proMMP9 independently of the engagement of C5a with its receptors expressed on inflammatory cells (FIG. 8D). The presence of an elevated level of C5b-9 together with the presence of multiple inflammatory mediators contributed to migration of inflammatory cells into the bronchial lumen in animals treated with anti-C5aR sIgG (FIG. 8C).

Both the adaptive and innate immune systems contributed in the complex process of the production and release of multiple inflammatory mediators, including leukotrienes, prostaglandins, histamine, alkaline proteins, cytokines, chemokines, and enzymes, which are responsible for bronchospasm, altered vascular permeability, adherence and migration of inflammatory cells, mucosal edema and excessive mucous secretion and ultimately lead to three unique but interdependent phenomena: airway inflammation, airway obstruction and AHR. Since there are many redundant biological mechanisms, under the right circumstances, such as in genetically deficient animals, these redundant mechanisms may compensate and contribute in a more significant fashion. The complex relationship and interactions of these components are responsible for airway inflammation, obstruction and AHR, as well as other pulmonary diseases or conditions.

Lung parenchymal cells possess the ability to produce C5 and cleave C5 into activated fragments (Desai et al, J. Exp. Pathol. (1984) 1:201-216). The activation of C5 as part of innate immune responses may well be an innocuous by-product of a self-defensive response, due in part to direct enzymatic cleavage of C5 (Maruo et al, J. Allergy Clin. Immunol. (1997) 100:253-260) after exposure to allergens (Nagata et al., supra), house dust (Maruo et al., supra), smoke (Robbins et al., Am. J. Physiol. (1991) 260:L254-L259.) or airway infections (Nagy et al., J. Allergy. Clin. Immunol. (2003) 112:729-734; Kasamatsu et al., Arerugi (1993) 42:1616-1622; Bjornson et al., Am. Rev. Respir. Dis. (1991) 143:1062-1066). The formation of intrapulmonary IC after allergen exposure may also activate complement cascade (Larsen, supra). This hypothesis proposes that activated C5 components are primarily located at the epithelial side of the airway and, in non-asthmatic individuals, the intrapulmonary activation of complement is well regulated (Varsano et al., Thorax (2000) 55:364-369). Consistent with this hypothesis, our data demonstrated that intrapulmonary C5 inhibition achieved similar efficacy as systemic C5 inhibition at checkpoint 3 (FIGS. 8A-8D) and at checkpoint 2. These data further suggest that intrapulmonary activated C5 components are major pro-inflammatory rather than anti-inflammatory forces.

The study also shows the effect of C5 inhibition on the inflammatory mediators produced or released by neutrophils or eosinophils (FIGS. 7A-7H). These inflammatory mediators, in particular TGF-β, RANTES and proMMP9, may cause irreversible damage to airways by inducing bronchial smooth muscle hypertrophy and deposition of collagen under the basal membranes of respiratory epithelium, which leads to the remodel and repair of lower airways, the focal point for those individuals with a poor long term prognosis (Boulet et al., Am. J. Respir. Crit. Care Med. (2000) 162:1308-1313). Accordingly, C5 inhibition, which utilizes a unique and different anti-inflammatory mechanism, may complement the potent anti-inflammatory effect of corticosteroid and other active agents, and have an added benefit for long term prognosis.

This study clearly demonstrates that the complex functional changes of airways seen in individuals with asthma coexist with the complex inflammatory processes. On one hand, activated C5 components, such as C5a through its binding with airway C5aR, serve as the direct link between the innate immune system and AHR. On the other hand, both C5a and C5b-9 regulate the downstream inflammatory cascade through their chemotactic and cell activation activities in the presence of IC and established airway inflammation. Blocking the generation of C5a and C5b-9 not only improves the functioning of lower airways but also ameliorates intrapulmonary inflammatory activities. In contrast, C5aR antagonist significantly improves functions of lower airways without a dramatic impact on intrapulmonary inflammatory activities.

Aerosol or Nebulization Compositions

In one respect, this application is directed to pulmonary drug delivery compositions and/or devices for delivering an antibody that inhibits the activation of the complement cascade. The pulmonary drug delivery compositions are useful for treating a pulmonary disease or condition. For example, aerosol compositions are provided for the delivery of an antibody or an antibody combined with an additional active agent to the respiratory tract. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung.

Pulmonary drug delivery may be achieved by inhalation, and administration by inhalation herein may be oral and/or nasal. Examples of pharmaceutical devices for pulmonary delivery include metered dose inhalers (MDIs), dry powder inhalers (DPIs), and nebulizers. Exemplary delivery systems by inhalation which can be adapted for delivery of the subject antibody and/or active agent are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the antibody and/or active agent are described in U.S. Pat. Nos. 6,294,153; 6,344,194; 6,071,497, and PCT applications WO02/066078; WO02/053190; WO01/60420; WO00/66206.

Pressurized metered dose inhalers (pMDIs) are the most commonly used inhaler worldwide. The aerosol is created when a valve is opened (usually by pressing down on the propellant canister), allowing liquid propellant to spray out of a canister. Typically, a drug or therapeutic is contained in small particles (usually a few microns in diameter) suspended in the liquid propellant, but in some formulations the drug or therapeutic may be dissolved in the propellant. The propellant evaporates rapidly as the aerosol leaves the device, resulting in small drug or therapeutic particles that are inhaled. Propellants typically used in such pMDIs include but are not limited to hydrofluoroalkanes (HFAs). A surfactant may also be used, for example, to formulate the drug or therapeutic, with pMDIs. Other solvents or excipients may also be employed with pMDIs, such as ethanol, ascorbic acid, sodium metabisulfate, glycerin, chlorobutanol, and cetylpyridium chloride. Such pMDIs may further include add-on devices such as, for example, spacers, holding chambers and other modifications.

Nebulizers produce a mist of drug-containing liquid droplets for inhalation. They are usually classified into two types: ultrasonic nebulizers and jet nebulizers. A new type of nebulizer is also available, which does not require ultrasound or air pressure to function. Single breath atomizers have also been developed (e.g., Respimat®), which is used to deliver a drug in a single inhalation and may be preferred because of less contamination. Jet nebulizers are more common and use a source of pressurized air to blast a stream of air through a drug-containing water reservoir, producing droplets in a complex process involving a viscosity-induced surface instability that leads to nonlinear phenomena in which surface tension and droplet breakup on baffles play a role. Ultrasonic nebulizers produce droplets by mechanical vibration of a plate or mesh. In either type of nebulizer, the drug is usually contained in solution in the liquid in the nebulizer and so the droplets being produced contain drug in solution. However, for some formulations (e.g., Pulmicort®) the drug is contained in small particles suspended in the water, which are then contained as particles suspended inside the droplets being produced. Certain excipients are usually included in formulations suitable for nebulization, such as sodium chloride (e.g., to maintain isotonicity), mineral acids and bases (e.g., to maintain or adjust pH), nitrogen headspace sparging, benzalkonium chloride, calcium chloride, sodium citrate, disodium edtate, and polysorbate 80.

The third type of inhaler is the dry powder inhaler (DPI). In DPIs, the aerosol is usually a powder, contained within the device until it is inhaled. The therapeutic or drug is manufactured in powder form as small powder particles (usually a few millionths of a meter, or micrometers, in diameter). In many DPIs, the drug or therapeutic is mixed with much larger sugar particles (e.g., lactose monohydrate), that are typically 50-100 micrometers in diameter. The increased aerodynamic forces on the lactose/drug agglomerates improve entrainment of the drug particles upon inhalation, in addition to allowing easier filling of small individual powder doses. Upon inhalation, the powder is broken up into its constituent particles with the aid of turbulence and/or mechanical devices such as screens or spinning surfaces on which particle agglomerates impact, releasing the small, individual drug powder particles into the air to be inhaled into the lung. The sugar particles are usually intended to be left behind in the device and/or in the mouth-throat.

One aspect of the application provides an aerosol composition comprising an antibody that inhibits activation of the complement cascade, wherein the composition is suitable for preventing or treating a pulmonary disease or condition in a subject. An aerosol antibody composition can be a composition comprising aerosolized antibody or a composition comprising an antibody in a formulation suitable for aerosolization. The antibody may be formulated in combination with an additional active agent, and the combination formulation is suitable for aerosolization. Alternatively, the antibody and an additional active agent may be formulated separately, such that they will be combined after aerosolization occurs or after being administered to a subject.

Another aspect of the application provides a nebulization composition comprising an antibody that inhibits activation of the complement cascade, wherein the composition is suitable for preventing or treating a pulmonary disease or condition in a subject. A nebulization antibody composition can be a composition comprising a nebulized antibody or a composition comprising an antibody in a formulation suitable for nebulization. Similarly, the antibody may be formulated in combination with an additional active agent, and the combination formulation is suitable for nebulization. Alternatively, the antibody and an additional active agent may be formulated separately, such that they will be combined after nebulization occurs or after being administered to a subject.

A further aspect of the application provides a biopharmaceutical package comprising an antibody that inhibits activation of the complement cascade and a nebulizer, wherein the package is suitable for preventing or treating a pulmonary disease or condition in a subject. The biopharmaceutical package may further comprise an active agent in addition to the antibody. The biopharmaceutical package may also comprise instructions for use.

An antibody of the present application can be specific to C5 such that it prevents the cleavage of C5 into C5a and C5b. The antibody can be specific to the C5 convertase. Alternatively, the antibody may be specific to a component of the complement system, for example, C5a, C5b, or C5b-9, and the antibody specific to the component preferably inhibits the component's function, for example, by blocking the component's binding to its respective receptor, or by blocking its function in activating subsequent signaling or events in the complement cascade. Certain embodiments employ eculizumab or pexelizumab, or both. An antibody or antibody therapeutic of the present application can be a full length immunoglobulin, a chimeric antibody (e.g., a humanized antibody), a single chain antibody, a domain antibody (e.g., a domain antibody as developed by Domantis, defined as the smallest functional binding units of antibodies, corresponding to the variable regions of either the heavy (VH) or light (VL) chains of human antibodies), an Fab fragment, or an antibody having an Fab fragment and a mutated Fc portion. In certain embodiments, the mutated Fc portion does not activate complement, or the mutation(s) in the Fc portion decreases the Fc portion's ability to activate complement. An antibody of the present application may be produced or processed in bulk and packaged in an ampule made of a suitable material (e.g., glass or plastic) at different doses. The antibody may be stable in a formulation at a concentration ranging from 1 mg/ml to 200 mg/ml.

An additional active agent (or an active agent in addition to the antibody therapeutic) of the present application can be another antibody therapeutic (e.g., an anti-complement or anti-C5 antibody, an anti-IgE antibody such as Xolair® or omalizumab, an anti-IL-4 antibody or an anti-IL-5 antibody), an anti-IgE inhibitor (e.g., Singulair® or montelukast sodium), a sympathomimetic (e.g., albuterol), an antibiotic (e.g., tobramycin), a deoxyribonuclease (e.g., Pulmozyme®), an anticholinergic drug (e.g., ipratropium bromide), a corticosteroid (e.g., dexamethasone), a β-adrenoreceptor agonist, a leukotriene inhibitor (e.g., zileuton), a 5 Lipoxygenase inhibitor, a PDE inhibitor, a CD23 antagonist, an IL-13 antagonist, a cytokine release inhibitor, a histamine H1 receptor antagonist, an anti-histamine, an anti-inflammatory agent (e.g. cromolyn sodium) or a histamine release inhibitor. As used herein, an active agent may also be referred to as a therapeutic or a drug.

An example of formulation suitable for aerosolization or nebulization of an antibody is in physiologic osmolarity (e.g., between 280 and 320 mM) at a suitable pH (e.g., pH 6 to 8). A formulation of the present application may further comprise an excipient, for example polysorbate 80 which can be used at 0.0015 to 0.02%.

U.S. Pat. No. 5,474,759 discloses aerosol formulations that are substantially free of chlorofluorocarbons, and having particular utility in medicinal applications. The formulations contain a propellant (such as 1,1,1,2,3,3,3,-heptafluoropropane), a medium-chain fatty acid propylene glycol diester, a medium-chain triglyceride, optionally a surfactant, and optionally auxiliary agents such as antioxidants, preservatives, buffers, sweeteners and taste masking agents.

Other pharmaceutically acceptable carriers may also be used in a formulation of the present application. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Methods of preparing these formulations or compositions include the step of bringing into association a compound of the present application with the carrier and, optionally, one or more accessory ingredients. In general, the formulations are prepared by uniformly and intimately bringing into association a compound of the present application with liquid carriers, or finely divided solid carriers, or both, and then, if necessary, shaping the product.

A nebulizer of the present application can be a jet air nebulizer (e.g., Pari LC® Jet Plus or Hudson T UP-DRAFT® II), an ultrasonic nebulizer (e.g., MABISMist II), a vibrating mesh nebulizer (e.g., MicroAir® by Omron) and a shockwave nebulizer (Evit Labs Sonik LDI20).

"Aerosol composition" means an antibody and/or an active agent described herein in a form or formulation that is suitable for pulmonary delivery. The aerosol composition may be in the dry powder form, it may be a solution, suspension or slurry to be nebulized, or it may be in admixture with a suitable low boiling point, highly volatile propellant. It is to be understood that more than one antibody and optionally other active agents or ingredients may be incorporated into the aerosolized formulation or aerosol composition and that the use of the term "antibody" or "active agent" in no way excludes the use of two or more such antibodies or other agents or ingredients.

In certain preferred embodiments, an antibody or active agent retains more than 50% of its activity after nebulization, preferably more than 70%. In certain preferred embodiments, an antibody or active agent retains more than 50% of its purity after nebulization, preferably more than 70%.

Active agent formulations suitable for use in the present application include dry powders, solutions, suspensions or slurries for nebulization and particles suspended or dissolved within a propellant. Dry powders suitable for use in the present application include amorphous active agents, crystalline active agents and mixtures of both amorphous and crystalline active agents. The dry powder active agents have a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders is >30%, usually >40%, preferably >50 and often >60% and the aerosol particle size distribution is about 1.0-5.0 μm mass median aerodynamic diameter (MMAD), usually 1.5-4.5 μm MMAD and preferably 1.5-4.0 μm MMAD. These dry powder active agents have a moisture content below about 10% by weight, usually below about 5% by weight, and preferably below about 3% by weight. Such active agent powders are described in WO 95/24183 and WO 96/32149, which are incorporated by reference herein.

Dry powder active agent formulations are preferably prepared by spray drying under conditions which result in a substantially amorphous powder. Bulk active agent, usually in crystalline form, is dissolved in a physiologically acceptable aqueous buffer, typically a citrate buffer having a pH range from about 2 to 9. The active agent is dissolved at a concentration from 0.01% by weight to 1% by weight, usually from 0.1% to 0.2%. The solutions may then be spray dried in a conventional spray drier available from commercial suppliers such as Niro A/S (Denmark), Buchi (Switzerland) and the like, resulting in a substantially amorphous powder. These amorphous powders may also be prepared by lyophilization, vacuum drying, or evaporative drying of a suitable active agent solution under conditions to produce the amorphous structure. The amorphous active agent formulation so produced can be ground or milled to produce particles within the desired size range. Dry powder active agents may also be in a crystalline form. The crystalline dry powders may be prepared by grinding or jet milling the bulk crystalline active agent.

The active agent powders of the present application may optionally be combined with pharmaceutical carriers or excipients which are suitable for respiratory and pulmonary administration. Such carriers may serve simply as bulking agents when it is desired to reduce the active agent concentration in the powder which is being delivered to a patient, but may also serve to improve the dispersability of the powder within a powder dispersion device in order to provide more efficient and reproducible delivery of the active agent and to improve handling characteristics of the active agent such as flowability and consistency to facilitate manufacturing and powder filling. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-.beta.-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate. sodium gluconate, tromethamin hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffinose, maltodextrins, glycine, sodium citrate, human serum albumin and mannitol.

The dry powder active agent formulations may be delivered using Inhale Therapeutic Systems' dry powder inhaler as described in WO 96/09085 which is incorporated herein by reference, but adapted to control the flow rate at a desirable level or within a suitable range. The dry powders may also be delivered using a metered dose inhaler as described by Laube et al. in U.S. Pat. No. 5,320,094, which is incorporated by reference herein.

Nebulized solutions may be prepared by aerosolizing commercially available active agent formulation solutions. These solutions may be delivered by a jet nebulizer such as the Raindrop, produced by Puritan Bennett, the use of which is described by Laube et al., supra. Other methods for delivery of solutions, suspensions of slurries are described by Rubsamen et al, U.S. Pat. No. 5,672,581. A device that uses a vibrating, piezoelectric member is described in Ivri et al., U.S. Pat. No. 5,586,550, which is incorporated by reference herein.

Propellant systems may include an active agent dissolved in a propellant or particles suspended in a propellant. Both of these types of formulations are described in Rubsamen et al., U.S. Pat. No. 5,672,581, which is incorporated herein by reference.

In certain embodiments, an aerosol or nebulization antibody composition can be combined with one or more other aerosol or nebulization treatments, such as sympathomimetics (e.g., albuterol), antibiotics (e.g., tobramycin), deoxyribonucleases (e.g., Pulmozyme®), anticholinergic drugs (e.g., ipratropium bromide), or corticosteroids.

In certain embodiments, an aerosol or nebulization antibody composition can be combined with one or more other therapies (concurrently or sequentially) administered via nebulization, inhalation, intravenous or oral routes, such as sympathomimetics (e.g., albuterol), anticholinergic drugs (e.g., ipratropium bromide), inflammation inhibitors (e.g., cromolyn sodium), leukotriene inhibitors (e.g., zileuton), anti-IgE inhibitors (e.g., Singulair®) or corticosteroids.

As described herein, an antibody or therapeutic may be formulated as microparticles. Microparticles having a diameter of between 0.5 and 10 microns can penetrate the lungs, passing through most of the natural barriers. A diameter of less than ten microns is generally required to bypass the throat; a diameter of 0.5 microns or greater is usually required to avoid being exhaled.

In certain embodiments, the subject antibody or therapeutic is formulated in a supramolecular complex, which may have a diameter of between 0.5 and 10 microns, which can be aggregated into particles having a diameter of between 0.5 and 10 microns.

In other embodiments, the subject antibodies or therapeutics are provided in liposomes or supramolecular complexes appropriately formulated for pulmonary delivery.

(i). Polymers for Forming Microparticles

In addition to the supramolecular complexes described above, a number of other polymers can be used to form the microparticles. As used herein, the term "microparticles" includes microspheres (uniform spheres), microcapsules (having a core and an outer layer of polymer), and particles of irregular shape.

Polymers are preferably biodegradable within the time period over which release of the antibody or therapeutic is desired or relatively soon thereafter, generally in the range of one year, more typically a few months, even more typically a few days to a few weeks. Biodegradation can refer to either a breakup of the microparticle, that is, dissociation of the polymers forming the microparticles and/or of the polymers themselves. This can occur as a result of change in pH from the carrier in which the particles are administered to the pH at the site of release, as in the case of the diketopiperazines, hydrolysis, as in the case of poly (hydroxy acids), by diffusion of an ion such as calcium out of the microparticle, as in the case of microparticles formed by ionic bonding of a polymer such as alginate, and by enzymatic action, as in the case of many of the polysaccharides and proteins. In some cases linear release may be most useful, although in others a pulse release or "bulk release" may provided more effective results.

Representative synthetic materials are: diketopiperazines, poly(hydroxy acids) such as poly(lactic acid), poly(glycolic acid) and copolymers thereof, polyanhydrides, polyesters such as polyorthoesters, polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, polyvinyl esters, polyvinyl halides, polyvinylpyrrolidone, polyvinylacetate, and poly vinyl chloride, polystyrene, polysiloxanes, polymers of acrylic and methacrylic acids including poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, and cellulose sulphate sodium salt, poly(butic acid), poly(valeric acid), and poly(lactide-co-caprolactone).

Natural polymers include alginate and other polysaccharides including dextran and cellulose, collagen, albumin and other hydrophilic proteins, zein and other prolamines and hydrophobic proteins, copolymers and mixtures thereof. As used herein, chemical derivatives thereof refer to substitutions, additions of chemical groups, for example, alkyl, alkylene, hydroxylations, oxidations, and other modifications in the art.

Bioadhesive polymers include bioerodible hydrogels described by H. S. Sawhney, C. P. Pathak and J. A. Hubell in Macromolecules, 1993, 26, 581-587, polyhyaluronic acids, casein, gelatin, glutin, polyanhydrides, polyacrylic acid, alginate, chitosan, and polyacrylates.

To further illustrate, the matrices can be formed of the polymers by solvent evaporation, spray drying, solvent extraction and other methods known to those skilled in the art. Methods developed for making microspheres for drug delivery are described in the literature, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988). The selection of the method depends on the polymer selection, the size, external morphology, and crystallinity that is desired, as described, for example, by Mathiowitz, et al., Scanning Microscopy 4, 329-340 (1990); Mathiowitz, et al., J. Appl. Polymer Sci. 45, 125-134 (1992); and Benita, et al., J. Pharm. Sci. 73, 1721-1724 (1984).

In solvent evaporation, described for example, in Mathiowitz, et al., (1990), Benita, and U.S. Pat. No. 4,272,398 to Jaffe, the polymer is dissolved in a volatile organic solvent. The antibody and/or therapeutic, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

In general, the polymer can be dissolved in methylene chloride. Several different polymer concentrations can be used, for example, between 0.05 and 0.20 g/ml. After loading the solution with drug, the solution is suspended in 200 ml of vigorously stirring distilled water containing 1% (w/v) poly(vinyl alcohol) (Sigma Chemical Co., St. Louis, Mo.). After four hours of stirring, the organic solvent will have evaporated from the polymer, and the resulting microspheres will be washed with water and dried overnight in a lyophilizer.

Microspheres with different sizes (1-1000 microns, though less than 10 microns for aerosol applications) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of antibodies or therapeutics, preferably sieved to appropriate size. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000.

In spray drying, the polymer is dissolved in an organic solvent such as methylene chloride (0.04 g/ml). A known amount of antibody and/or therapeutic is suspended (if insoluble) or co-dissolved (if soluble) in the polymer solution. The solution or the dispersion is then spray-dried. Microspheres ranging in diameter between one and ten microns can be obtained with a morphology which depends on the selection of polymer.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., Pharmazeutische Industrie 40-111A, 1230 (1978). The advantage of this system is the ability to further modify the surface of the microspheres by coating them with polycationic polymers such as polylysine, after fabrication, for example, as described by Lim, et al., J. Pharm. Sci. 70, 351-354 (1981). For example, in the case of alginate, a hydrogel can be formed by ionically crosslinking the alginate with calcium ions, then crosslinking the outer surface of the microparticle with a polycation such as polylysine, after fabrication. The microsphere particle size will be controlled using various size extruders, polymer flow rates and gas flow rates.

Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethyleneimine (PEI) can be prepared to reduce the amount of carboxyl groups on the alginate microcapsules.

(ii). Pharmaceutical Compositions

The microparticles can be suspended in any appropriate pharmaceutical carrier, such as saline, for administration to a patient. In the most preferred embodiment, the microparticles will be stored in dry or lyophilized form until immediately before administration. They can then be suspended in sufficient solution, for example an aqueous solution for administration as an aerosol, or administered as a dry powder.

(iii). Targeted Administration

The microparticles can be delivered to specific cells or organ, especially phagocytic cells and organs. Where systemic delivery of the drug or therapeutic is desirable, endocytosis of the microparticles by macrophages in the lungs can be used to target the microparticles to the spleen, bone marrow, liver, lymph nodes, and other parts of the body.

The microparticles can also be targeted by attachment of ligands, such as those described above, which specifically or non-specifically bind to particular targets, for example, particular targets within the pulmonary system or associated with a pulmonary disease or condition (e.g., a target specific for cancerous cells in the lung). Examples of such ligands also include antibodies and fragments including the variable regions, lectins, and hormones or other organic molecules having receptors on the surfaces of the target cells.

(iv). Storage of the Microparticles

In certain embodiments, the microparticles are stored lyophilized. The dosage is determined by the amount of encapsulated antibodies and/or therapeutics, the rate of release within the pulmonary system, and the pharmacokinetics of the antibodies and/or therapeutics.

(v). Delivery of Microparticles

The microparticles can be delivered using a variety of methods, ranging from administration directly into the nasal passages so that some of the particles reach the pulmonary system, to the use of a powder instillation device, to the use of a catheter or tube reaching into the pulmonary tract. As described above, dry powder inhalers are commercially available, although those using hydrocarbon propellants are no longer used and those relying on the intake of a breath by a patient can result in a variable dose. Examples of suitable propellants include hydrofluoroalkane propellants, such as 1,1,1,2-tetrafluoroethane (CF3CH2F) (HFA-134a) and 1,1,1,2,3,3,3-heptafluoro-n-propane (CF3CHFCF3) (HFA-227), perfluoroethane, monochloroifluoromethane, 1,1 difluoroethane, and combinations thereof.

Therapeutic Methods

A first aspect of the application provides a method for preventing or treating a pulmonary disease or condition in a subject comprising administering to the subject a therapeutically effective amount of an antibody that inhibits activation of the complement cascade. In certain embodiments, an additional active agent is also administered to the same subject. Administration of the antibody and the additional active agent may occur simultaneously or sequentially in either order.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition (e.g., asthma) in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

Pulmonary diseases or conditions contemplated by the application include, but are not limited to, asthma, bronchial constriction, bronchitis, a chronic obstructive pulmonary disease (COPD), interstitial lung diseases, lung malignancies, α-1 anti-trypsin deficiency, emphysema, bronchiectasis, bronchiolitis obliterans, sarcoidosis, pulmonary fibrosis, and collagen vascular disorders.

The subject or patient receiving this treatment is any animal in need, including primates, in particular humans, and other mammals such as equines, cattle, swine and sheep, and poultry and pets in general.

The phrase "therapeutically effective amount" as used herein means that amount of a compound, material, or composition comprising a compound of the present invention which is effective for producing some desired therapeutic effect by inhibiting C5 or activation of the complement cascade in at least a sub-population of cells or an organ in an animal and thereby blocking the biological consequences of that function in the treated cells or an organ, at a reasonable benefit/risk ratio applicable to any medical treatment.

The timing of administering a therapeutic to a subject can vary, for example, depending on the identity of the subject or the pulmonary disease or condition to be treated or prevented, or both. For example, the administration may occur before the manifestation of the pulmonary condition (e.g., pre-asthmatic attack or pre-bronchial constriction), during the manifestation of the pulmonary condition (e.g., during the asthmatic attack or bronchial constriction), or after the manifestation of the pulmonary condition (e.g., post-asthmatic attack or post-bronchial constriction).

The phrase "inhibits the activation of complement cascade" refers to any inhibitory effect or action on any component of the complement system as described above conferred by an antibody or active agent of the present application. The inhibitory effect may be manifested by decrease in or lack of a response typical to activation of complement. For example, typical cellular and other biological responses to activation of complement include, but are not limited to, release of histamine, smooth muscle contraction, increased vascular permeability, leukocyte activation, chemotaxis (e.g., movement of granulocytes to the site of complement activation), and other inflammatory phenomena including cellular proliferation. In certain embodiments, the inhibitory effect is specific to the C5 component. In certain embodiments, the inhibitory effect is specific to C5 convertase, for example, blocking C5 convertase's function to convert C5 into C5a and C5b-9. In certain embodiments, the inhibitory effect is specific to C5a. In certain embodiments, the inhibitory effect is specific to C5b or C5b-9.

EXAMPLES

The following examples are offered by way of illustration and not by way of limitation.

Materials and Methods

Animals: Male C5s BALB/cByJ, C57BL/6J mice and C5d B10D2oSn/J, AKR/J and SWR/J mice were purchased from the Jackson Laboratory and housed in a pathogen free facility. In addition to serum C5b-9 mediated hemolysis, the C5 genotype was further confirmed by PCR performed on tail DNA using a pair of primers (5'-CAC GAT AAT GGG AGT CAT CTG GG-3' (SEQ ID NO:1) and 5'-AAG TTG GAG TGT GGT CTT TGG GCC-3' (SEQ ID NO:2) that amplify a 280-bp DNA fragment from both C5s and C5d DNA. This fragment encodes a HindIII site that is selectively destroyed by a mutation in the C5 gene, such that HindIII (New England BioLabs, Mass.) digestion selectively cleaves the C5s but not the C5d PCR products into 150 and 130-bp fragments. All animal protocols were reviewed by Institutional Committee and were in accordance with NIH guidelines.

Reagents: Anti-mouse C5 mAb (BB5.1) (Wang et al., Proc. Natl. Acad. Sci. U.S.A. (1996) 93:8563-8568) and an isotype matched irrelevant control mAb (HFN7.1), which is specific to human fibronectin, were purified from ascites. BB5.1 Fab, which was purified with a kit (Pierce Biotechnology), had retained similar activity of BB5.1 and was more than 97% in purity. The anti-C5aR sIgG, which was shown to prevent mortality in experimental sepsis (Riedemann et al., J. Clin. Invest. (2002) 110:101-108), was able to prevent zymosan induced neutrophil migration. Both anti-C5aR sIgG and the control sIgG were purified from sera harvested from C5aR deficient mice (Gerard et al., Curr. Opin. Immunol. (2002) 14:705-708) that were repeatedly immunized with either PBS or peptide spanning the N-terminus of the mouse C5aR and one extra cysteine (Riedemann et al., supra) emulsified with CFA. Antibodies from either ascites or serum samples were purified by protein A affinity chromatography (Amersham). Corticosteroid (dexamethasone) was purchased from Sigma. Recombinant mouse C5a, which was free of endotoxin contamination and had potent chemotactic activity in neutrophil migration assay, was cloned and purified as previously reported (Riedemann et al., supra).

Induction of Airway Inflammation and Severe Airway Response

BALB/c and B10D2oSn Mice 10-12 wks of age were sensitized on day 1 and day 14 with i.p. injection of 20 μg OVA (Grade V; Sigma) emulsified in 2 mg aluminum hydroxide (Alum Inject; Pierce Biotechnology). Mice were immunized with 1% OVA for 10 min via airway on days 28, 29 and 30 with a jet nebulizer (Harvard Apparatus) connected to a single housing chamber (Buxco Electronics, Inc.). On day 32, all sensitized animals were aerosol challenged with 5% OVA for 10 min. In checkpoint 3 experiments, BALB/c mice were aerosol challenged with 5% OVA again on day 35. Sham C5s or C5d mice were immunized with Alum only and aerosol challenged with PBS instead of OVA.

Non-Invasive Measurement of sRaw sRaw, which measures the resistance of both upper and lower airways, was measured by a DCP in conscious animals with spontaneous breathing (Buxco). The DCP was used to monitor the longitudinal changes of sRaw prior to and after each 5% OVA aerosol challenge. In checkpoint 3 experiments, a DCP was used to ensure the appearance of EAR prior to randomizing animals into different treatment groups.

Invasive Measurement of Lower Airway Functions

Changes in RL and Cdyn were measured by using Buxco Biosystem software and a Buxco whole body plethysmograph. Mice were anesthetized (Avertin, 160 mg/kg) and tracheas cannulated. Spontaneous breathing was blocked by pancuronium bromide (0.3 mg/kg i.p.). Respirations were maintained by a Harvard Apparatus Inspira ventilator, which calculated a tidal volume and respiratory rate according to body weight. Measurements of RL and Cdyn were performed during the peak of LAR, 5 h after aerosol challenge with 5% OVA. Real-time changes of RL and Cdyn were recorded by Buxco software and reported as the mean value of five min of recording. AHR was evaluated based on changes of RL and Cdyn during aerosol Mch challenges. Changes in RL and Cdyn were expressed as a percentage of baseline after each aerosol challenge. A Buxco aerosol control and sonicating nebulizer unit was attached to the ventilator for aerosol delivery of Mch through tracheal cannulation. PBS or Mch (1.6 mg/ml) was delivered at the rate of 10 puffs or 20 puffs per 10 seconds, with each puff of aerosol delivery lasting 15 ms.

C5 Inhibition (1) For C5 inhibition at checkpoint 1, anti-C5 mAb (BB5.1) or a control mAb (HFN7.1) was administered i.p. at 40 mg/kg on days 25, 29, and 31. Dexamethasone (2 mg/kg) was used as a positive control. (2) Animals that experienced airway response to 5% OVA provocation on day 32 were randomized for the following studies. For C5 inhibition at checkpoint 2, animals were given one i.p. injection of either dexamethasone (2 mg/kg), anti-C5 mAb (40 mg/ml) or control mAb (40 mg/kg) on day 33. On day 35, animals were anesthetized and tracheas cannulated for measurement of RL and Cdyn during aerosol Mch challenges. (3) At checkpoint 3, anti-C5 mAb (40 mg/kg), control mAb (40 mg/kg), or dexamethasone (2 mg/kg) was administered by i.v. injection 20 min after aerosol challenging animals with 5% OVA on day 35. For intrapulmonary C5 inhibition at this critical point, animals were given aerosol administration of either anti-C5 mAb (3 mg/ml), anti-C5 Fab (3 mg/ml), control mAb (3 mg/ml), anti-C5aR sIgG (3 mg/ml), control sIgG (2 mg/ml), or corticosteroid (2 mg/ml) for 10-30 min by using a jet nebulizer connected to a single chamber housing the animal. Sham-immunized mice were given sham treatment with the same volume of PBS solution administered through the same route. The results from three intrapulmonary C5 inhibition experiments, which were conducted with identical protocols, were pooled together.

Analysis of Bronchoalveolar Lavage Fluid (BALF)

Approximately 5.5 h after allergen provocation, after the measurement of RL and Cdyn, BALF was harvested by instilling 1 ml PBS through the tracheal cannula, followed by gentle aspiration. The BALF was resuspended in 400 μl PBS. The total numbers of WBC in BALF were counted by using a hemocytometer or an automatic cell counter as in the aerosol experiments (Cell-Dyn 3700 Abbott). Cytospin slides were prepared, fixed and stained using Diff-Quik (VWR International, Inc.). The WBC differential was determined by a certified pathologist after counting a total of 300 WBC per slide on a 100× microscopic lens. The BALF levels of proMMP9, activated TGF-β, RANTES, eotaxin and IL-13 (R&D Systems, Inc.), IL-5 (Amersham Pharmacia Biotech, Inc.), and histamine (Immunotech, Inc.) were measured by ELISA according to the manufacturer's instructions.

Analysis of Serum OVA Specific Antibodies

Serum samples were harvested 5 h after 5% allergen provocation on day 32 for OVA specific IgG and IgE by ELISA.

Lung Histology

Lung was inflated with 10% buffered formalin (1 ml) through tracheal cannulation and fixed in 10% formalin at least 24 h. Lung samples were stained with Giemsa. Double blind histological analysis was performed to quantify airway inflammation according to the following criteria. 0: No detectable airway inflammation; 1: Less than 25% bronchials and surrounding vasculature were found with either perivascular or peribronchial inflammatory cell infiltration; 2: Approximately 25-50% of bronchials and surrounding vasculature were affected; 3: Approximately 50-75% bronchials and surrounding vasculature were affected; 4: >75% of bronchials and surrounding vasculature were affected.

C5b-9 Mediated Hemolytic Assay and In Vitro C5a Mediated Neutrophil Migration Assay Serum harvested at the indicated time was used as the source of C5b-9, which mediated the hemolysis of chicken RBC as previously reported (Wang et al., supra). Mouse sera (Sigma) were incubated with either BB5.1 (100 μg/ml) or the same volume of PBS prior to activation with zymosan (1 mg/ml; Sigma). Diluted sera (20%) were used as the source of C5a for neutrophil chemotaxis experiments.

Statistical Analysis

The data were expressed as the means±S.E.M. Student's one-tailed t-test assuming equal variance was used (MS Windows). A P value less than 0.05 was considered significant.

Blocking the Generation of C5a and C5b-9 by Anti-C5 mAb, BB5.1

Figure 1B:
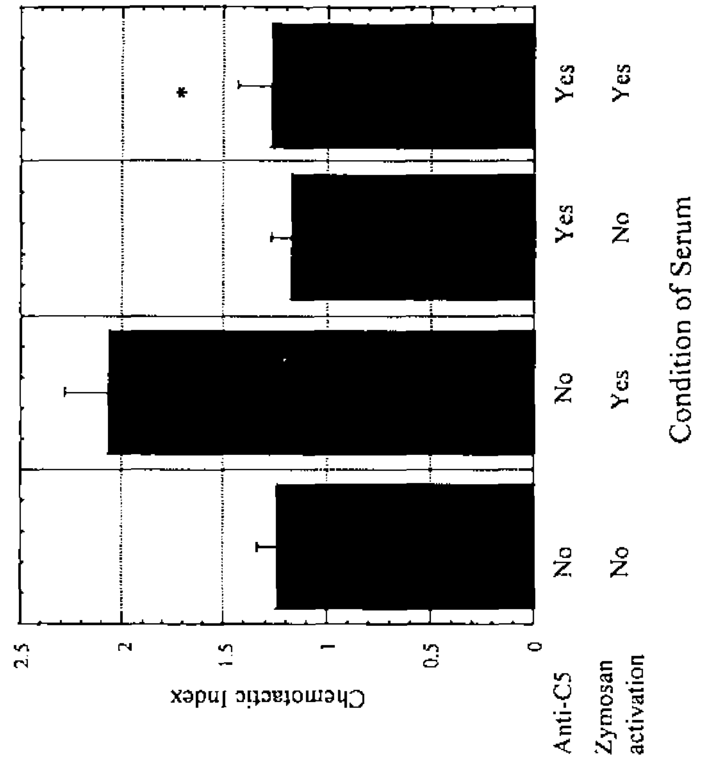
FIGS. 1A-1B illustrate blocking the generation of C5a and C5b-9 by anti-C5 mAb, BB5.1. Pharmacodynamic profile (FIG. 1A) of inhibition of C5b-9 mediated hemolysis from animals given a single i.v. or i.p. injection of anti-C5 mAb (40 mg/kg) or control mAb (40 mg/kg). ● represents data from 4 control animals that were given control mAb by either i.v. (n=2) or i.p. (n=2). ▲ represents i.p. anti-C5 mAb-treated animals (n=3). Δ represents i.v. anti-C5 mAb-treated animals (n=3). C5a-mediated neutrophil migration (FIG. 1B) was analyzed in an in vitro assay. Zymosan activated sera (20%) was used as the source of C5a. Anti-C5 mAb (100 μg/ml) was added to serum sample prior to zymosan activation as indicated (n=8). * indicates $p<0.05$ when compared to zymosan activated serum samples. BALB/c mice were used in all figures except FIGS. 4C and 4D.
Figure 1A:
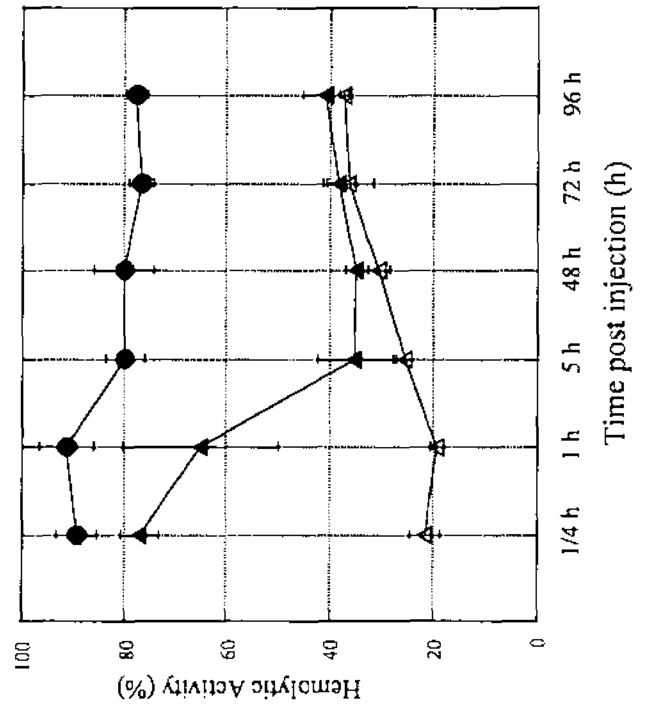

Functional inhibition of complement component C5 by anti-C5 mAb was determined by the pharmacodynamic profile of blocking serum C5b-9 mediated hemolytic activity (FIG. 1 A). In addition, C5a mediated neutrophil migration was determined in an in vitro assay (FIG. 1 B). The pharmacodynamics of C5 inhibition by a single i.v. injection of anti-C5 mAb, BB5.1, is very different from the pharmacodynamics of a single i.p. injection during the first 5 h after administration. More than 80% of C5b-9 mediated hemolysis was inhibited within 1 h of i.v. administration of BB5.1, compared to less than 30% of inhibition by i.p. injection. Administration of anti-C5 mAb continued blocking more than 60% of hemolysis between 5 h and 48 h after i.v. injection while approximately 56% of hemolysis was blocked during this period of time after i.p. injection. Serum samples harvested from control mAb treated mice had more than 80% of normal hemolytic activity during the entire period of the study (FIG. 1 A). Hemolytic activity gradually returned to the normal range one wk after a single injection of anti-C5 mAb.

An in vitro neutrophil migration assay was employed to test the ability of anti-C5 mAb on blocking the generation of C5a (FIG. 1 B). Inhibition of serum samples with anti-C5 mAb prior to zymosan activation significantly blocked human neutrophil chemotaxis which was mediated by the presence of C5a after zymosan activation, as seen in zymosan activated control sera (FIG. 1, B). Since anti-C5 mAb, BB5.1, blocked the generation of both C5a and C5b-9 and did not bind to C5a directly, this anti-C5 mAb is probably specific to blocking cleavage of C5 by C5 convertase.

Figure 2A:
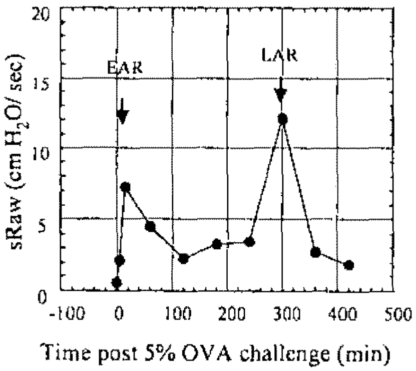
FIGS. 2A-2B show airway responses to OVA provocation and definition of three critical checkpoints.
Figure 2B:
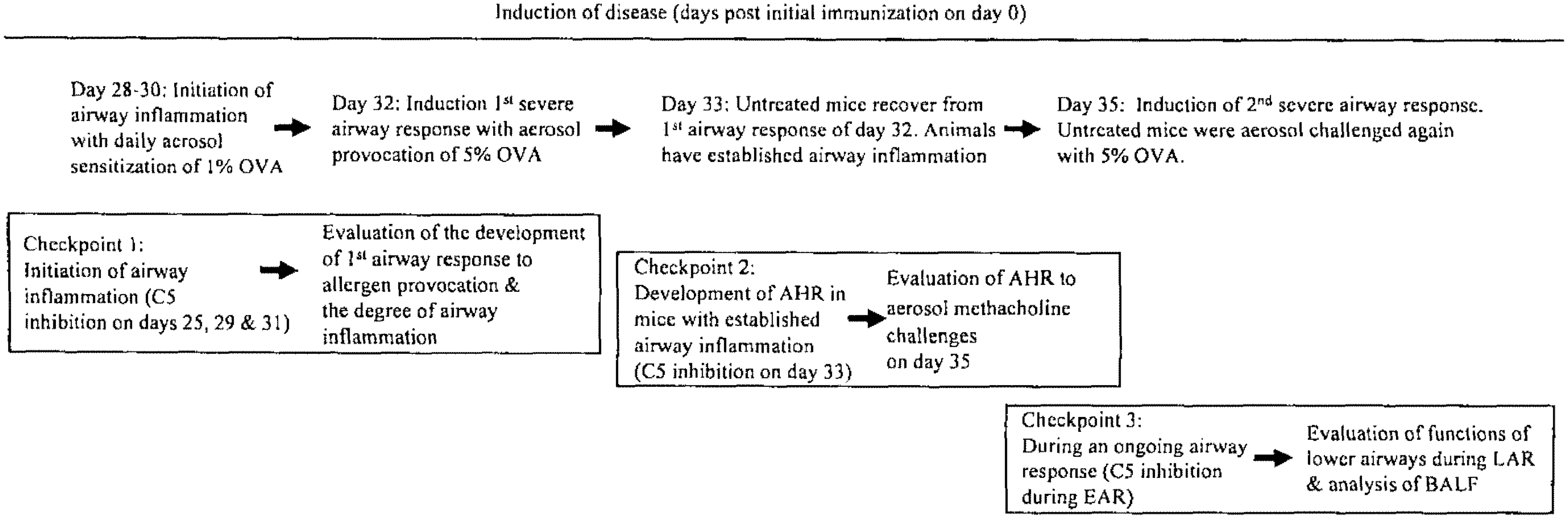

Development of Severe Airway Response in OVA Sensitized Animals and Definition of Three Critical Points OVA-sensitized animals immediately developed a severe airway response after aerosol challenge with 5% OVA (FIG. 2A). A typical airway response to aerosol provocation with allergen consisted of an early-phase airway response (EAR), which is known to be mediated by the release of histamine by mast cells, and a late-phase airway response (LAR), which is mediated by the combination of effects of infiltration of inflammatory cells, edema and bronchial constriction (Larsen, Annu. Rev. Immunol. (1985) 3:59-85). The airway response after 5% OVA provocation was monitored by a non-invasive double chamber plethysmograph (DCP) in each mouse to measure the longitudinal changes of specific airway response (sRaw), which indicates the appearance of EAR and LAR (FIG. 2A). EAR was typically a brief elevation of sRaw 15 min after 5% OVA provocation and LAR was typically observed 5 h later, consistent with an earlier report (Cieslewicz et al., J. Clin. Invest. (1999)104: 301-308). Both EAR and LAR have magnitudes between 5 to 30 fold over the baseline. The severe airway response during the peak of LAR was generally evident as animals showed obvious labored breathing. Since inhibition of C5 can be achieved by the administration of anti-C5 mAb, we sought to dissect the critical involvement of C5 and its activated components at three critical points (FIG. 2B) during critical stages of the disease. The three critical checkpoints are: 1) initiation of airway inflammation, one of the two hallmarks of asthma's pathogenesis; 2) development of AHR to nonspecific stimuli, another hallmark of asthma; and 3) sustainment of an on-going airway response after allergen provocation. Both checkpoint 2 and checkpoint 3 are designed to evaluate the contribution of C5 in subjects that had experienced severe airway response previously (FIG. 2B) and had established airway inflammation. Checkpoint 3 studies were conducted during an on-going airway response after allergen provocation by administering treatment via either an i.v. or aerosol route during the EAR. Functions of lower airways and quantification of airway inflammation were evaluated during the peak of LAR, 5 h after 5% OVA provocation.

Checkpoint 1: Involvement of C5 in the Initiation of Airway Inflammation

Figure 3A:
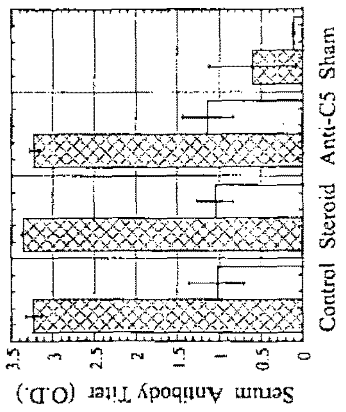
FIGS. 3A-3H show contributions of C5 at checkpoint 1, the initiation of airway inflammation. Mean serum OVA-specific antibody titers of 5-6 mice on day 32 were measured by ELISA (FIG. 3A). Cross hatched bars: OVA-specific IgG. Open bars: OVA-specific IgE. Also on day 32, animals were trachea cannulated for the measurement of RL (FIG. 3B) and Cdyn (FIG. 3C) 5 h after 5% aerosol OVA provocation, followed by histological analyses of lung (FIG. 3D). The mean histology score for control mAb-treated mice (FIG. 3F) is 2±0.28 compared to 0.64±0.21 for corticosteroid-treated animals (FIG. 3G) and 1.25±0.25 for anti-C5 mAb-treated animals (FIG. 3H) compared to total lack of inflammation, score=0, seen in sham-mice (FIG. 3E). * indicates $p<0.05$ when comparing treated animals (i.e. corticosteroid or anti-C5 mAb treatment) with control mAb treated animals, while—indicates $p<0.05$ when comparing corticosteroid treated mice with animals treated with antibody targeting C5 or C5aR in this and all following figures unless otherwise indicated. For clarity, all control mAb treated animals are labeled as control in all following figures. Arrow indicates eosinophil infiltration. Giemsa stain, magnification=100×.
Figure 3B:
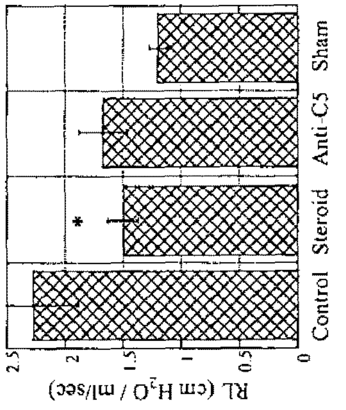
Figure 3C:
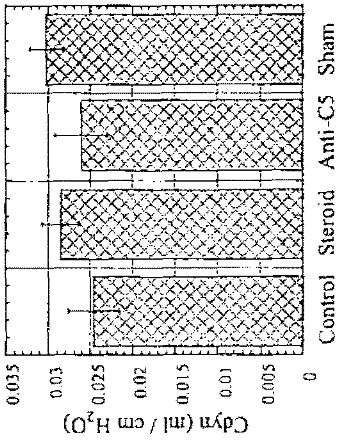
Figure 3D:
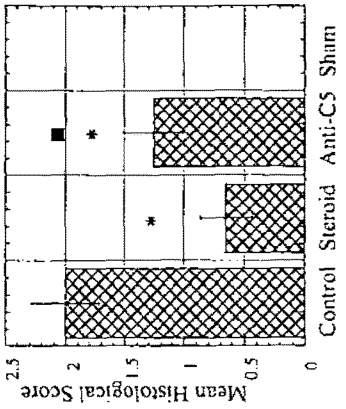
Figure 3E:

C5 inhibition at checkpoint 1, at the time of repeat aerosol sensitization of 1% OVA, had no significant impact on serum levels of OVA-specific IgE or IgG on day 32 (FIG. 3A). Corticosteroid treated mice also had elevated levels of OVA-specific IgE and IgG, that may have been generated long before the corticosteroid or anti-C5 mAb was administered on day 25. Sham treated mice had a negligible level of OVA specific IgG or IgE. As a result of repeated administration (i.p.) of anti-C5 mAb, approximately 80% of C5b-9 mediated hemolysis was inhibited on day 32 (21.1%±4) as compared to the normal hemolytic activity seen in control mAb and corticosteroid treated mice (92.7%±6.8). Two key functions of lower airways were examined by tracheal cannulation at 5 h after 5% OVA provocation. The increase in lung resistance (RL) is commonly associated with significant obstruction of lower airways (FIG. 3B) and a decrease in the dynamic lung compliance (Cdyn) is associated with the loss of lung elasticity, an important characteristic of the return to normal volume after pressure changes seen in a normal lung (FIG. 3C). The significantly increased RL and reduced Cdyn seen in control mAb-treated mice indicated an increased airway obstruction (FIGS. 3 B and C). Sham-mice provided normal ranges of RL and Cdyn at 5 h after exposure to aerosol PBS solution.

Figure 3F:
Figure 3G:
Figure 3H:

Correlating to its potent anti-inflammatory and anti-asthmatic activities, corticosteroid treatment at checkpoint 1 significantly blocked the increase of RL and prevented the loss of Cdyn. Similarly, C5 inhibition at checkpoint 1 markedly reduced the increase of RL 5 h after allergen provocation with an RL of 1.66 cm $H_2O$/ml/second ±0.2, compared to an RL of 2.17 cm H2O/ml/second ±0.33 seen in control mAb treated animals (FIG. 3B). C5 inhibition also slightly reduced the loss of Cdyn (FIG. 3C). Double blind histological analysis (FIG. 3D) of lung tissue confirmed data from the function analysis and demonstrated that control mAb-treated BALB/c mice had severe perivascular and peribronchial infiltration of inflammatory cells (FIG. 3F). A significant reduction of histology score was observed in corticosteroid treated mice (FIG. 3G) while less impressive reduction was observed in anti-C5 mAb-treated mice (FIG. 3H). Similar to severe allergic asthma in humans, eosinophils were the predominant inflammatory cells (more than 50%) in the perivascular and peribronchial lesions along the airways (FIGS. 3F-3H).

Checkpoint 2: Contribution of C5 in the Development of AHR in Animals with Established Airway Inflammation In addition to airway inflammation, AHR to non-specific stimuli is another hallmark of asthma. AHR was evaluated as changes of RL and Cdyn expressed as a percentage of baseline in response to increasing doses of aerosol methacholine (Mch) challenges (FIGS. 4 A and B). Control mAb-treated BALB/c mice had significant increases of RL and significant losses of Cdyn during the course of aerosol Mch challenges, while sham-mice responded only modestly to aerosol Mch challenges. Two of eight among control mAb-treated mice died during high doses of aerosol Mch challenge due to severe respiratory stress. In contrast, C5 inhibition prevented dramatic increases of RL and the reduction of Cdyn during the course of aerosol Mch challenges, similar to those animals treated with corticosteroid (FIGS. 4 A and B). The loss of Cdyn and increase of RL during the course of aerosol Mch challenges compared to sham-mice were probably due to the presence of established airway inflammation in these animals. There were no noticeable differences in the degree of airway inflammation among the three treated cohorts. Anti-C5 mAb treated mice had approximately 45% of normal hemolytic activity on day 35.

In order to compare our results of C5 inhibition at checkpoint 2 with data from a previous report (Karp et al., Nat. Immunol. (2000) 1:221-226), the presence or absence of native intrinsic AHR was examined in some strains of normal C5d mice as previously reported (De Sanctis et al., Am. J. Respir. Crit. Care Med. (1997) 156:S82-S88; Levitt et al., FASEB J. (1998) 2:2605-2608). Non-immunized C5d AKR/J mice have dramatic airway responses to increasing doses of aerosol Mch challenges with significant increases of RL over baseline (84.2%±16.7 with 20 puffs Mch) and a significant reduction of Cdyn under baseline (40%±5.4 with 20 puffs of Mch) whereas C5d SWR/J and B10D2oSn mice have minimal changes of RL and Cdyn, indistinguishable from C5 sufficient (C5s) BALB/c mice and C57BL/6 mice, with no more than a maximal change of 15% of either RL or Cdyn away from baseline (n=3 for each strain, data not shown). Next, C5d B10D2oSn mice, which do not have intrinsic AHR, were immunized and challenged with aerosol Mch in the identical manner as C5s BALB/c mice in FIGS. 4 A and B. Subgroups of sensitized C5d animals were also given either control or anti-C5 mAb treatment on day 33. C5d B10D2oSn mice developed a similar degree of airway inflammation as C5s mice, with an average histology score of 1.91±0.37 (n=6) compared to a histology score of 2.25±0.25 in C5s BALB/c mice (n=4). No noticeable histological difference was observed between anti-C5 mAb and control mAb treated C5d mice. In contrast to a previous report (Karp et al., supra), increasing doses of aerosol Mch challenges did not induce significant changes of lower airway functions in OVA immunized B10D2.oSn mice (FIGS. 4 C and D). Treatment with either anti-C5 mAb or control mAb on day 33 had no impact on the development of AHR. The data from both mAb treated cohorts were pooled together as an mAb treated cohort (FIGS. 4 C and D). Furthermore, reconstitution of OVA immunized B10D2.oSn mice with recombinant mouse C5a (rmC5a) completely restored AHR in response to aerosol Mch challenge as indicated by the significant increase of RL and reduction of Cdyn (FIGS. 4 C and D).

Reconstitution of rmC5a was not sufficient for the development of AHR since sham-B10D2.oSn mice reconstituted with rmC5a did not have significant changes of lower airway functions during Mch challenge (FIGS. 4 C and D). Analysis of serum samples harvested from each mouse after Mch challenges confirmed the C5 deficient status of B10D2.oSn mice with average hemolytic activity of 8.1%±0.9 compared to 108%±3.8 of C5s BALB/c mice. Furthermore, random tail samples (n=2) from each lot of C5s and C5d animals were analyzed to confirm the C5 genotype status.

Checkpoint 3: Contribution of C5 During an On-Going Airway Response

The role of C5 in sustaining an on-going airway response was also examined. Intervention was given during the peak of EAR, which was monitored by DCP at 15 min after aerosol exposure to 5% OVA on day 35. All control mAb-treated BALB/c mice developed severe LAR with significant increases of RL and reductions of Cdyn 5 h after allergen provocation (FIGS. 5 A and B).

Figure 5B:
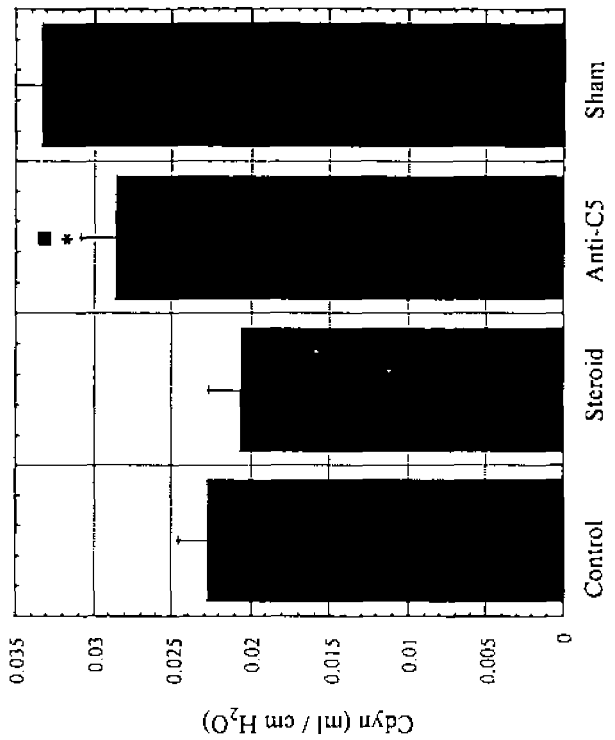
FIGS. 5A-5B show contributions of C5 at checkpoint 3, during an on-going airway response. Animals that experienced previous airway response to allergen provocation on day 32 were given a second aerosol allergen challenge on day 35. During the peak of EAR, animals were randomized and given (i.v.) the indicated treatment. Animals were trachea cannulated for the measurement of RL (FIG. 5A) and Cdyn (FIG. 5B) 5 h after the OVA provocation. (n=7-8 mice per group.)

Administration of treatment through i.v. injection during EAR was selected to achieve rapid systemic C5 inhibition, which completely blocked the development of LAR with minimal increase of RL 5 h after 5% OVA provocation (FIG. 5A) and prevented much of the loss of lung elasticity indicated by the minimal reduction of Cdyn (FIG. 5B). Interestingly, corticosteroid treatment did not eliminate the development of LAR with significant elevation of RL and reduction of Cdyn at 5 h.

Although no immediate impacts (within 5 h) on lower airway functions were observed after i.v. corticosteroid treatment (FIG. 5A), this treatment significantly modulated the intrapulmonary IL-13 (FIG. 7B) and significantly improved lower airway functions 24 h later. Double blind histologic analysis of lung tissue showed comparable levels of perivascular and peribronchial infiltration of inflammatory cells from the animals 5 h after i.v. intervention with either corticosteroid, anti-C5 mAb or control mAb, similar to the histological sample shown in FIG. 3F.

Effect of C5 Inhibition on the Migration of Inflammatory Cells

Figure 5A:
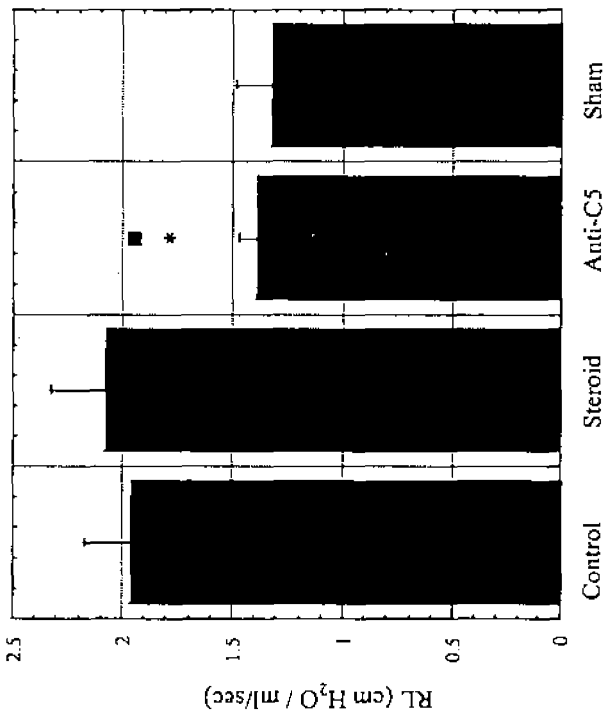

The migration of inflammatory cells from airway tissue inflammation into bronchial lumen as enumerated was also examined by bronchial alveolar lavage fluid (BALF) WBC analysis. There was a significant reduction of total BALF inflammatory cells in anti-C5 mAb-treated BALB/c mice compared to control mAb-treated mice at checkpoint 1 (FIG. 6A). The blockade on the migration of inflammatory cells by C5 inhibition exceeded the degree of improved lower airway function (FIGS. 3 B and C) and reduced tissue inflammation (BRIEF D). Similarly, when BALF was harvested at checkpoint 3 (FIG. 6B), C5 inhibition again had significant blockade on the migration of inflammatory cells into bronchial lumen, with significantly lower BALF WBC counts in anti-C5 treated animals than in animals treated with either corticosteroid or control mAb. This result is in dramatic contrast to the prominent presence of perivascular and peribronchial infiltration of inflammatory cells in lung tissue harvested before allergen provocation on day 35. The significant blockade on the migration of inflammatory cells by C5 inhibition correlated with the significantly enhanced efficacy of C5 inhibition over corticosteroid therapy at checkpoint 3 (FIGS. 5A and B).

Figure 6C:
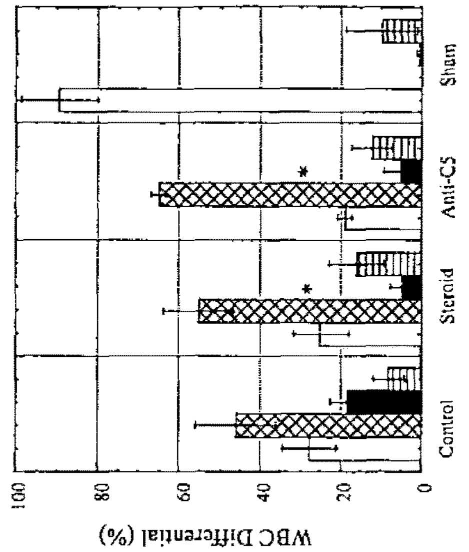
FIGS. 6A-6C show BALF WBC counts and differential analysis. BALF was obtained 5 h after aerosol allergen provocation at checkpoint 1 (FIG. 6A) or at checkpoint 3 (FIGS. 6B-6C). Total BALF WBC counts (FIGS. 6A-6B) and their differential analyses (FIG. 6C) were performed by a pathologist in a double blind fashion. For 6 (FIG. 6C), open bars: alveolar macrophages. Cross hatched bars: Eosinophils. Solid bars: Neutrophils. Hatched bars: Lymphocytes. (n=6-8 mice per group.)
Figure 6B:
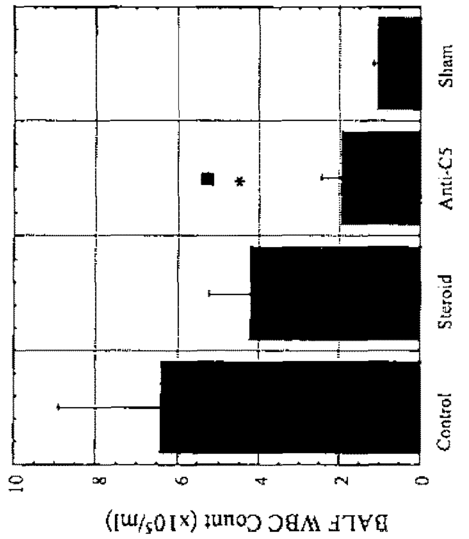
Figure 6A:
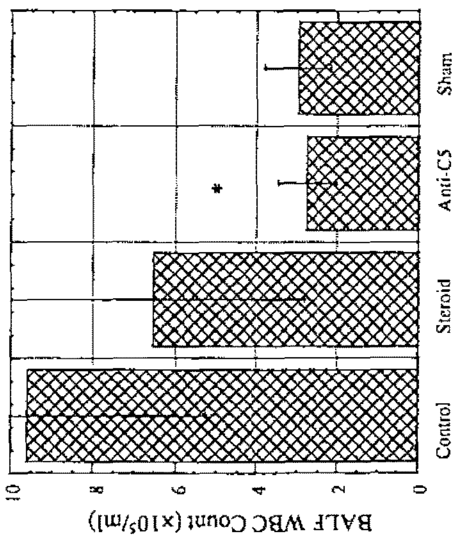

Sham mice provided the baseline level of BALF WBC counts, which are primarily normal alveolar macrophages (82.3%±10.3) in WBC differential analysis (FIG. 6C). Eosinophils constituted more than 45% of BALF inflammatory cells from all OVA immunized animals, regardless of the therapeutic intervention. There was a significant reduction in the percentage of neutrophils recovered in BALF from the animals treated at checkpoint 3 with either corticosteroid (4.5%±2.8) or anti-C5 mAb (6.3%±3.3) versus control mAb treated mice (18.3%±4.4). No significant reductions occurred in the percentages of eosinophils or lymphocytes in BALF samples from the animals given intervention at checkpoint 3 (FIG. 6C).

Figure 7A:
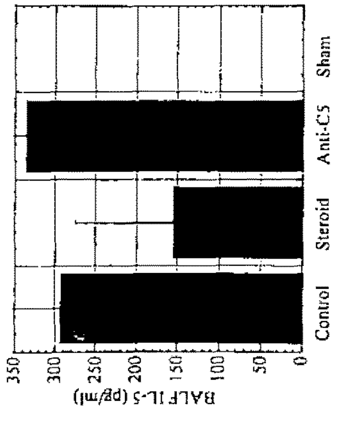
FIGS. 7A-7H show BALF levels of inflammatory mediators. BALF was obtained 5 h after aerosol allergen provocation at checkpoint 1 (cross hatched bars) or checkpoint 3 (solid bars). BALF levels of IL-5 (FIG. 7A), IL-13 (FIG. 7B), histamine (FIG. 7C), eotaxin (FIG. 7D), RANTES (FIG. 7E), activated TGF-β (FIG. 7F), TNF-α (FIG. 7G) and proMMP9 (FIG. 7H) were measured by ELISA. (n=6-8 samples per group.)
Figure 7B:
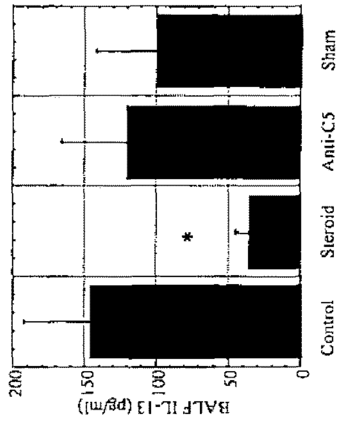
Figure 7C:
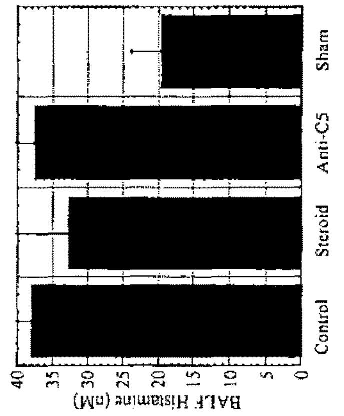
Figure 7D:
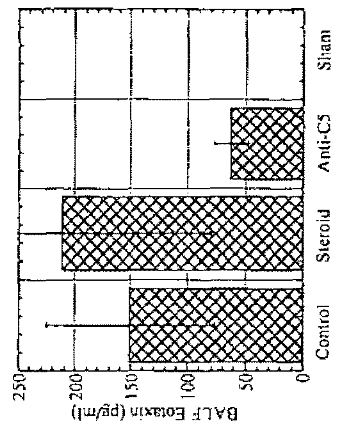
Figure 7E:
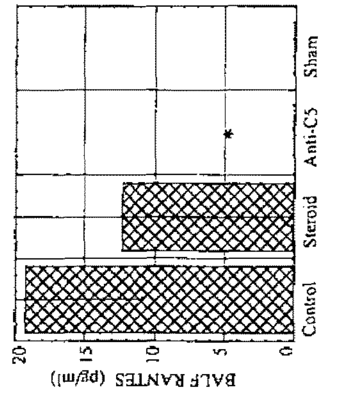
Figure 7F:
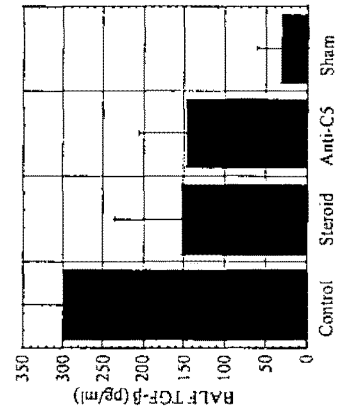
Figure 7G:
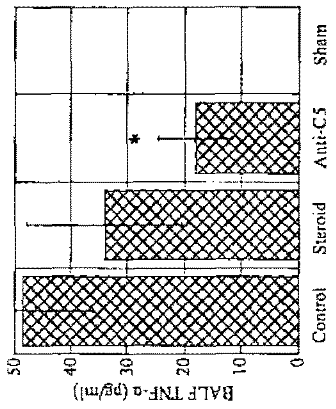

Effect of C5 Inhibition on Intrapulmonary Th1/Th2 Cytokine Profile and Inflammatory Mediators BALF harvested from control mAb treated mice had markedly increased levels of IL-5 and IL-13 (FIGS. 7 A and B) as compared to sham mice. Corticosteroid treatment markedly reduced the BALF levels of IL-5 and IL-13, however, this did not translate into an immediate improvement of lower airway function (FIGS. 5 A and B) during the 5 h period of treatment. The dramatic improvement of lower airway functions (FIGS. 5 A and B) seen after C5 inhibition at checkpoint 3 did not correlate with any reduction of BALF level of IL-5 and IL-13. The statistical difference of the BALF level of IL-13 between anti-C5- and corticosteroid-treated mice equals a p value of 0.051 C5 inhibition or corticosteroid therapy at checkpoint 3 did not influence the BALF level of histamine (FIG. 7C). This was expected since histamine had probably already been released into the airway lumen upon the engagement of IgE receptors of mast cells by aerosol allergen provocation and was responsible for the appearance of EAR when therapeutic intervention was given. Eosinophils, the most prominent inflammatory cells along lower airways (FIGS. 3F-3H), are probably responsible for the production of eotaxin, RANTES and TGF-β (FIGS. 7D-7F) in asthmatic individuals. Control mAb-treated animals had significantly elevated BALF levels of eotaxin (FIG. 7D), RANTES (FIG. 7E), or activated TGF-β (FIG. 7F), compared to negligible or non-detectable levels of these mediators in sham-mice. In contrast, C5 inhibition had a marked impact on BALF levels of eotaxin, RANTES, and activated TGF-β when given either at checkpoint 1 (FIGS. 7D and 7E) or checkpoint 3 (FIG. 7F). Corticosteroid treatment only reduced the BALF level of TGF-β when given at checkpoint 3 but had no obvious impact on the production and release of eotaxin or RANTES when given at checkpoint 1.

Figure 7H:
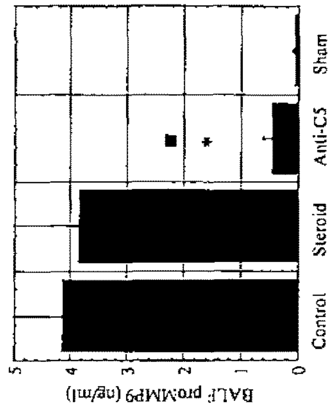

Neutrophils are commonly believed to be responsible for the production of bronchial TNF-α and proMMP9. C5 inhibition significantly reduced BALF levels of TNF-α (FIG. 7G) when given at checkpoint 1, significantly different from control mAb-treated mice. The bronchial level of proMMP9 was dramatically reduced and was significantly different from control mAb-treated and corticosteroid-treated mice when C5 inhibition was given at checkpoint 3 (FIG. 7H).

Checkpoint 3: Contribution of Intrapulmonary Activation of C5 During an On-Going Airway Response The massive migration of inflammatory cells from airway tissue inflammation into bronchial lumen probably results from powerful chemotactic forces from the epithelial mucosa of the airway. Thus, C5 may be activated intrapulmonarily during an airway response to allergen provocation. The functions of lower airways and parameters of inflammation were evaluated after blocking the intrapulmonary activation of C5. The potential impact at checkpoint 3 by inhibitory receptors, such as FcγRIIB (Katz, Curr. Opin. Immunol. (2002) 14:698-704; Ravetch et al., Annu. Rev. Immunol. (2001) 19:275-90), were also evaluated, as the result of interaction between intrapulmonary C5 and anti-C5 mAb and the subsequent formation of immune complexes (IC).

Effect of intrapulmonary C5 inhibition with anti-C5 mAb was directly compared to anti-C5 Fab in order to achieve this goal. Furthermore, the efficacy of an anti-C5aR serum IgG (sIgG) was evaluated in order to dissect the role of intrapulmonary C5a versus C5b-9 at this checkpoint. As demonstrated in FIGS. 8 A and B, control mAb-treated animals developed severe LAR with significant increases of RL and significant reductions of Cdyn, in significant contrast to the normal RL and Cdyn seen in sham-mice. Aerosol administration of corticosteroid blocked the development of LAR as evidenced by the reduction of RL with corresponding preservation of Cdyn. Blocking intrapulmonary C5 activation with aerosol administration of either anti-C5 mAb or anti-C5 Fab during the peak of EAR also prevented the development of LAR with minimal increase of RL and minimal reduction of Cdyn (FIGS. 8 A and B). RL and Cdyn of both anti-C5 treated cohorts were significantly different from control mAb treated animals. Blocking the binding of intrapulmonary C5a to its receptors with an anti-C5aR sIgG also prevented the development of LAR with minimal increase of RL and minimal reduction of Cdyn similar to animals treated with anti-C5 mAb. There was no statistical difference between the three cohorts treated with either anti-C5 mAb, anti-C5 Fab, or anti-C5aR sIgG (FIGS. 8 A and B).

When the parameters of intrapulmonary inflammatory activities were examined, such as the migration of inflammatory cells (FIG. 8C) and the BALF level of proMMP9 (FIG. 8D), significant differences were found between blocking intrapulmonary activation of C5 versus blocking the binding of C5a to its C5aR. Aerosol administration of either anti-C5 mAb or its Fab fragment during EAR significantly blocked both the migration of inflammatory cells into bronchial airway lumen and the elevation of BALF level of proMMP9, whereas blocking the engagement of C5aR had no significant impact on these two key inflammatory parameters similar to the animals treated with control mAb (FIGS. 8 C and D). Consistent with its ability to block the development of LAR (FIGS. 8 A and B), aerosol administration of corticosteroid also ameliorated intrapulmonary inflammatory activities with marked reduction of the migration of inflammatory cells and the production of proMMP9 (FIGS. 8 C and D) indicating the importance of inflammatory activities at the epithelial side of the bronchial lumen. Aerosol administration of anti-C5 mAb, anti-C5 Fab or anti-C5aR sIgG did not have any impact on serum C5b-9 mediated hemolytic activity.

Combination Therapy:

As demonstrated in FIG. 9, animals treated with a non-specific control antibody had significant increases of lung resistance during the course of Mch challenges. In this study, two animals challenged with high doses of Mch died due to severe respiratory stress. In contrast, both the steroid and anti-C5 treated animals have only moderate increases of lung resistance, higher than normal sham immunized animals but significantly lower than control placebo treated mice. Combined treatment with both anti-C5 antibody and steroid significantly further reduced the increases of lung resistance during the course of Mch challenges. Based on this result, both steroid and C5 inhibitor can prevent the development of airway hyper-responsiveness to non-specific aerosol stimuli in asthmatic individuals with established airway inflammation.

Nebulization Formulations

Examples of formulations suitable for nebulization of an antibody are shown in FIG. 10. Specifically, as shown in FIG. 10, "Formulation 1" is 30 mg/ml of an antibody, 10 mM sodium phosphate, 150 mM NaCl, and 0.001 to 0.02%

Tween 80 by volume. “Formulation 2” is 40-200 mg/ml of an antibody, 20 mM histidine, 50 mM glycine, 3% (w/v) sorbital, 1.5% (w/v) mannitol, and 0.001 to 0.02% Tween 80. FIG. 11 further demonstrates the effectiveness of nebulization treatment. The results shown in FIG. 11 were obtained following a study that employed the same protocol as the Checkpoint 2 study described herein, except that the treatment here was delivered by nebulization on day 32 instead of i.p. For anti-C5 antibody, 3 mg/ml of BB5.1 was subject to 10 min nebulization, and 2 mg/ml steroid was also subject to 10 min nebulization. For the combination therapy, the final concentrations subjected to 10 min nebulization were: 3 mg/ml for BB5.1 and 2 mg/ml for the steroid.

FIG. 12 further shows that eculizumab in Formulation 1 (FIG. 10) at 30 mg/ml can be effectively and efficiently nebulized by a conventional nebulizer such as the Pari LC Jet Plus or a specialty nebulizer such as Sonik LDI. FIG. 12 shows that a majority of the particles after nebulization were less than 5 μM, which is suitable for deep lung delivery.

As shown in FIG. 13, eculizumab in Formulation 1 (FIG. 10) can be effectively and efficiently delivered by a conventional nebulizer, comparable to the aerosol characteristics of an existing pulmonary drug delivered by inhalation, Pulmozyme®, also using a conventional nebulizer. Eculizumab in Formulation 1 (FIG. 10) can also be effectively and efficiently delivered by a specialty nebulizer, for example, Sonik LDI.

Using SDS-PAGE and HPLC analyses, FIG. 14 and FIG. 15 demonstrate that eculizumab can be effectively and efficiently delivered by nebulization. Eculizumab in a suitable formulation was nebulized using either the Pari-Jet Air nebulizer or the Sonik LDI nebulizer. The nebulized antibody, in a spray form, was collected from the mouth piece of the nebulizer (e.g., F1D2F), and different sizes of mouth pieces (e.g., F1D2C1-C5) were used. The SDS-PAGE and HPLC analyses demonstrated the integrity of the nebulized antibody through various sizes of the spray mouth piece, as shown by the purity of the samples analyzed.

REFERENCES

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the application described herein. Such equivalents are intended to be encompassed by the following claims.

I claim:

1. A pharmaceutical composition comprising an anti-05 antibody, sodium phosphate at a concentration of 10 mM, sodium chloride at a concentration of 150 mM, and polysorbate 80 at a level of 0.001 to 0.02% by volume, wherein the anti-05 antibody comprises a variable light chain CDR1 comprising amino acid residues 26-36 of SEQ ID NO:1, a variable light chain CDR2 comprising amino acid residues 52-58 of SEQ ID NO:1, a variable light chain CDR3 comprising amino acid residues 91-99 of SEQ ID NO:1, a variable heavy chain CDR1 comprising amino acid residues 152-161 of SEQ ID NO:1, a variable heavy chain CDR2 comprising amino acid residues 176-192 of SEQ ID NO:1, and a variable heavy chain CDR3 comprising amino acid residues 225-237 of SEQ ID NO:1.

2. The pharmaceutical composition of claim 1, wherein the pH of the composition is between pH 6 and pH 8.

3. The pharmaceutical composition of claim 2, wherein the composition has physiologic osmolality.

4. A pharmaceutical composition comprising an anti-05 antibody, sodium phosphate at a concentration of 10 mM, sodium chloride at a concentration of 150 mM, and polysorbate 80 at a level of 0.001 to 0.02% by volume, wherein the anti-05 antibody comprises a heavy chain variable region comprising residue numbers 1-122 of SEQ ID NO: 2 and a light chain variable region comprising residue numbers 1-108 of SEQ ID NO: 3.

5. The pharmaceutical composition of claim 4, wherein the pH of the composition is between pH 6 and pH 8.

6. The pharmaceutical composition of claim 5, wherein the composition has physiologic osmolality.

* * * * *